United States Patent US 10,767,153 B2
Dalby et al. Sep. 8, 2020

(54) MECHANICAL BIOREACTOR

(71) Applicants: THE UNIVERSITY COURT OF THE UNIVERSITY OF GLASGOW, Glasgow, Strathclyde (GB); UNIVERSITY OF THE WEST OF SCOTLAND, Paisley Renfrewshire (GB)

(72) Inventors: Matthew Dalby, Strathclyde (GB); Habib Nikukar, Strathclyde (GB); Gabriel Pemberton, Stevenage (GB); Adam Curtis, Strathclyde (GB); Stuart Reid, Renfrewshire (GB); Peter Childs, Renfrewshire (GB)

(73) Assignees: THE UNIVERSITY COURT OF THE UNIVERSITY OF GLASGOW, Glasgow (GB); THE UNIVERSITY OF THE WEST OF SCOTLAND, Paisley (GB)

(*) Notice: Subject to any disclaimer, the term of this patent is extended or adjusted under 35 U.S.C. 154(b) by 146 days.

(21) Appl. No.: 15/759,388

(22) PCT Filed: Aug. 19, 2016

(86) PCT No.: PCT/EP2016/069700
§ 371 (c)(1),
(2) Date: Mar. 12, 2018

(87) PCT Pub. No.: WO2017/029393
PCT Pub. Date: Feb. 23, 2017

(65) Prior Publication Data
US 2018/0251719 A1 Sep. 6, 2018

(30) Foreign Application Priority Data
Aug. 19, 2015 (GB) .................................. 1514734.1

(51) Int. Cl.
C12M 1/42 (2006.01)
C12M 3/00 (2006.01)
(Continued)

(52) U.S. Cl.
CPC ............. *C12M 35/04* (2013.01); *C12M 21/08* (2013.01); *C12M 23/12* (2013.01); *C12M 41/46* (2013.01); *C12M 27/16* (2013.01)

(58) Field of Classification Search
CPC .............................. C12M 35/04; C12M 23/12
(Continued)

(56) References Cited

U.S. PATENT DOCUMENTS

| 2013/0052254 A1 | 2/2013 | Arinzeh et al. |
| 2014/0038257 A1* | 2/2014 | Subramanian ......... C12N 13/00 435/173.8 |
| 2017/0248583 A1* | 8/2017 | Simmons ............. C12N 5/0075 |

FOREIGN PATENT DOCUMENTS

| CN | 104513784 A | 4/2015 |
| DE | 102012015999 A1 | 11/2013 |
| EP | 2538989 B1 | 3/2014 |

OTHER PUBLICATIONS

Wu et al., Low-Magnitude High-Frequency Vibration Inhibits RANKL-Induced Osteoclast Differentiation of RAW264.7 Cells, 2012, International Journal of Medical Sciences, 9(9), pp. 801-807 (Year: 2012).*

(Continued)

*Primary Examiner* — Kevin Joyner
*Assistant Examiner* — Holly Kipouros
(74) *Attorney, Agent, or Firm* — Troutman Pepper Hamilton Sanders LLP

(57) ABSTRACT

A mechanical bioreactor for transferring vibrations to cell cultures for the purpose of stimulating various biological processes across a relatively large (relative to the amplitude (Continued)

of the vibrations) sample receiving surface. This bioreactor allows multiple samples to receive identical stimulation, which may enable the process to be significantly scaled up. The invention may be particularly applicable to nanoscale vibration amplitudes, where it is non-trivial to design a device that performs this function, because many materials exhibit natural deformation on a scale that would mask or inhibit transfer of nanoscale vibration energy.

21 Claims, 17 Drawing Sheets

(51) Int. Cl.
    *C12M 1/32*      (2006.01)
    *C12N 13/00*     (2006.01)
    *C12M 1/34*      (2006.01)
    *C12M 3/06*      (2006.01)

(58) Field of Classification Search
    USPC ...................................................... 435/289.1
    See application file for complete search history.

(56) References Cited

OTHER PUBLICATIONS

Kang et al., Effects of combined mechanical stimulation on the proliferation and differentiation of pre-osteoblasts, 2011, Experimental and Molecular Medicine, 43(6), pp. 367-373. (Year: 2011).*
GB Search Report dated Jun. 15, 2016 in GB Application No. 1514734.1. 3 pages.
Nikukar et al., "Osteogenesis of Mesenchymal Stem Cells by Nanoscale Mechanotransduction," 2013, ACS Nano, vol. 7, No. 3, pp. 2758-2767. 13 pages.
PCT International Search Report dated Dec. 13, 2016 in International Application No. PCT/EP2016/069700. 3 pages.
Pemberton et al., "Nanoscale Stimulation of Osteoblastogenesis from Mesenchymal Stem Cells: Nanotopography and Nanokicking," Mar. 2015, Future Medicine, vol. 10, No. 4, pp. 547-560. 14 pages.
Berry et al., "The Interaction of Human Bone Marrow Cells With Nanotopographical Features in Three Dimensional Constructs," Journal of Biomedical Materials Research Part A, 2006, 79A(2): pp. 431-439. 9 pages.
Burack et al., "The Activating Dual Phosphorylation of MAPK by MEK is Nonprocessive," Biochemistry, 1997, 36 (20): pp. 5929-5933. 5 pages.
Celil et al., "BMP-2 and Insulinlike Rowth Factor-I Mediate Osterix (Osx) Expression in Human Mesenchymal Stem Cells via the MAPK and Protein Kinase D Signaling Pathways," Journal of Biological Chemistry, 2005, 280(36): pp. 31353-31359. 8 pages.
Chan et al., "The Effects of Microporosity on Osteoinduction of Calcium Phosphate Bone Graft Substitute Biomaterials," Acta Biomater, 2012, 8(7): pp. 2788-2794. 7 pages.
Cheng et al., "Osteoinduction of Calcium Phosphate Biomaterials in Small Animals," Mater Sci Eng C Mater Biol Appl, 2013, 33(3): pp. 1254-1260. 7 pages.
Conrad et al., "Adult Stem Cell Lines in Regenerative Medicine and Reconstructive Surgery," Journal of Surgical Research, 2005, 124(2): pp. 201-208. 8 pages.
Curtis et al., "Cell Interactions at the Nanoscale: Piezoelectric Stimulation," IEEE Trans Nanobioscience, 2013, 12(3): pp. 247-254. 8 pages.
Dalby, M.J., "Cellular Response to Low Adhesion Nanotopographies," International Journal of Nanomedicine, 2007, 2(3): pp. 373-381. 10 pages.
Dalby et al., "Genomic Expression of Mesenchymal Stem Cells to Altered Nanoscale Topographies," Journal of the Royal Society Interface, 2008, 5(26): pp. 1055-1065. 11 pages.
Dalby et al., "Nanotopographical Stimulation of Mechanotransduction and Changes in Interphase Centomere Positioning," Journal of Cellular Biochemistry, 2007, 100(2): pp. 326-338. 14 pages.
Engler et al., "Matrix Elasticity Directs Stem Cell Lineage Specification," Cell 126, 2006, pp. 677-689. 13 pages.
Gaston et al., "The Response of Vocal Fold Fibroblasts and Mesenchymal Stromal Cells to Vibration," PLoS ONE, 2012, 7(2): p. e30965. 9 pages.
Habibovic et al., "Osteoinduction by Biomaterials—Physicochemical and Structural Influences," J Biomed Mater Res A, 2006, 77(4): pp. 747-762. 16 pages.
Henstock et al., "Cyclic Hydrostatic Pressure Stimulates Enhanced Bone Development in the Foetal Chick Femur in Vitro," Bone, 2013, 53(2): pp. 468-477. 10 pages.
Ingber, D., "How Cells (Might) Sense Microgravity," The FASEB Journal, 1999, 13(9001): pp. 3-15. 13 pages.
Ito et al., "Effects of Vibration on Differentiation of Cultured PC12 Cells," Biotechnol Bioeng, 2011, 108(3): pp. 592-599. 8 pages.
Jeong et al., "Bromopropane Compounds Inhibit Osteogenesis by ERK-Dependent Runx2 Inhibition in C2C12 Cells," Archives of Pharmacal Research, 2014, 37(2): pp. 276-283. 8 pages.
Kacena et al., "Experiments with Osteoblasts Cultured Under Hypergravity Conditions," Microgravity Sci Technol, 2004, 15(1): pp. 28-34. 7 pages.
Kilian et al., "Geometric Cues for Directing the Differentiation of Mesenchymal Stem Cells," Proc Natl Acad Sci USA, 2010, 107(11): pp. 4872-4877. 6 pages.
Kim et al., "ERK 1/2 Activation in Enhanced Osteogenesis of Human Mesenchymal Stem Cells in Poly(Lacticglycolic Acid) by Cyclic Hydrostatic Pressure," Journal of Biomedical Materials Research Part A, 2007, 80A(4): pp. 826-836. 11 pages.
Kim et al., "Human Mesenchymal Stromal Cells are Mechanosensitive to Vibration Stimuli," J Dent Res, 2012, 91(12): pp. 1135-1140. 6 pages.
Kingham et al., "Nanotopographical Cues Augment Mesenchymal Differentiation of Human Embryonic Stem Cells," Smal 1, 2013, 9(12): pp. 2140-2151. 12 pages.
Kozawa et al., "Divergent Regulation by p44/p42 MAP Kinase and p38 MAP Kinase of Bone Morphogenetic Protein-4-Stimulated Osteocalcin Synthesis in Osteoblasts," Journal of Cellular Biochemistry, 2002, 84(3): pp. 583-589. 7 pages.
Lan Levengood et al., "The Effect of BMP-2 on Micro- and Macroscale Osteointegration of Biphasic Calcium Phosphate Scaffolds With Multiscale Porosity," Acta Biomater, 2010, 6(8): pp. 3283-3291. 9 pages.
Liu et al., "Hydrostatic Pressures Promote Initial Osteodifferentiation with ERK1/2 not p38 MAPK Signaling Involved," J Cell Biochem, 2009, 107(2): pp. 224-232. 9 pages.
Luu et al., "Mechanical Stimulation of mesenchymal Stem Cell Proliferation and Differentiation Promotes Osteogenesis While Preventing Dietary-Induced Obesity," J Bone Miner Res, 2009, 24(1): pp. 50-61. 13 pages.
Macagno et al., "FAK Acts as a Suppressor of RTK-MAP Kinase Signalling in *Drosophila* Melanogaster Epithelia and Human Cancer Cells," Plos Genetics, 2014, 10(3). 17 pages.
Mammoto et al., "A Mechanosensitive Transcriptional Mechanism That Controls Angiogenesis," Nature, 2009, 457 (7233): pp. 1103-U57. 7 pages.
Miyakoshi, J., "The Review of Cellular Effects of a Static Magnetic Field," Science and Technology of Advanced Materials, 2006, 7(4): pp. 305-307. 4 pages.
Pemberton et al., "Nanoscale Stimulation of Osteoblastogenesis from Mesenchymal Stem Cells: Nanotopography and Nanokicking," Nanomedicine 2015, vol. 10, No. 4, pp. 547-560. 14 pages.
Prodanov et al., "Substrate Nanotexture and Hypergravity Through Centrifugation Enhanced Initial Osteoblastogenesis," Tissue Eng Part A, 2013, 19(1-2): pp. 114-124. 12 pages.
"Properties of Piezo Actuators—Dynamic Operation," Cited Aug. 2014, Available from http://piceramic.com/en/piezo-technology/properties-piezo-actuators/dynamic-operation/. 3 pages.
Salter et al., "Electrophysiological Responses of Human Bone Cells to Mechanical Stimulation: Evidence for Specific Integrin Function

(56) References Cited

OTHER PUBLICATIONS in Mechanotransduction," Journal of Bone and Mineral Research, 1997, 12(7): pp. 1133-1141. 9 pages.

Sawada et al., "Force Transduction by Triton Cytoskeletons," J Cell Biol, 2002, 156(4): pp. 609-615. 7 pages.

Tirkkonen et al., "The Effects of Vibration Loading on Adipose Stem Cell Number, Viability and Differentiation Towards Bone-Forming Cells," JR Soc Interface, 2011, 8(65): pp. 1736-1747. 12 pages.

Vogel et al., "Local Force and Geometry Sensing Regulate Cell Functions," Nat Rev Mol Cell Biol, 2006, 7(4): pp. 265-275. 11 pages.

Wehland et al., "The Impact of Altered Gravity and Vibration on Endothelial Cells During a Parabolic Flight," Cell Physiol Biochem, 2013, 31 (2-3): pp. 432-451. 20 pages.

Wen et al., "Interplay of Matrix Stiffness and Protein Tethering in Stem Cell Differentiation," Nat Mater, 2014. 9 pages.

Wysocki et al., "Whole-Body Vibration Therapy for Osteoporosis: State of the Science," Ann Intern Med, 2011, 155 (10): pp. 680-686, W206-13. 15 pages.

Xu et al., "Salvianolic Acid B Promotes Osteogenesis of Human Mesenchymal Stem Cells Through Activating ERK Signaling Pathway," International Journal of Biochemistry & Cell Biology, 2014, 51: pp. 1-9. 9 pages.

Zhang et al., "Effects of Mechanical Vibration on Proliferation and Osteogenic Differentiation of Human Periodontal Ligament Stem Cells," Arch Oral Biol, 2012, 57(10): pp. 1395-1407. 13 pages.

Zhao et al., "The MEK5/ERK5 Pathway Mediates Fluid Shear Stress Promoted Osteoblast Differentiation," Connect Tissue Res, 2014, 55(2): pp. 96-102. 8 pages.

Zhu et al., "The Transcription Factor Osterix (SP7) Regulates BMP6-Induced Human Osteoblast Differentiation," Journal of Cellular Physiology, 2012, 227(6): pp. 2677-2685. 9 pages.

\* cited by examiner

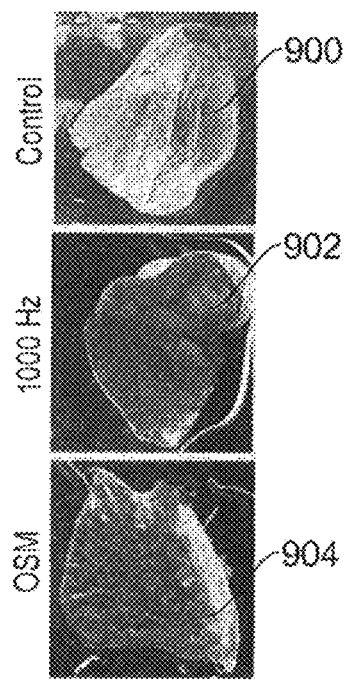
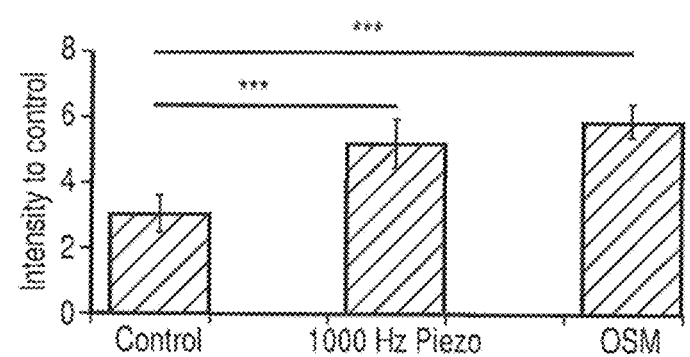
FIG. 11A
FIG. 11B
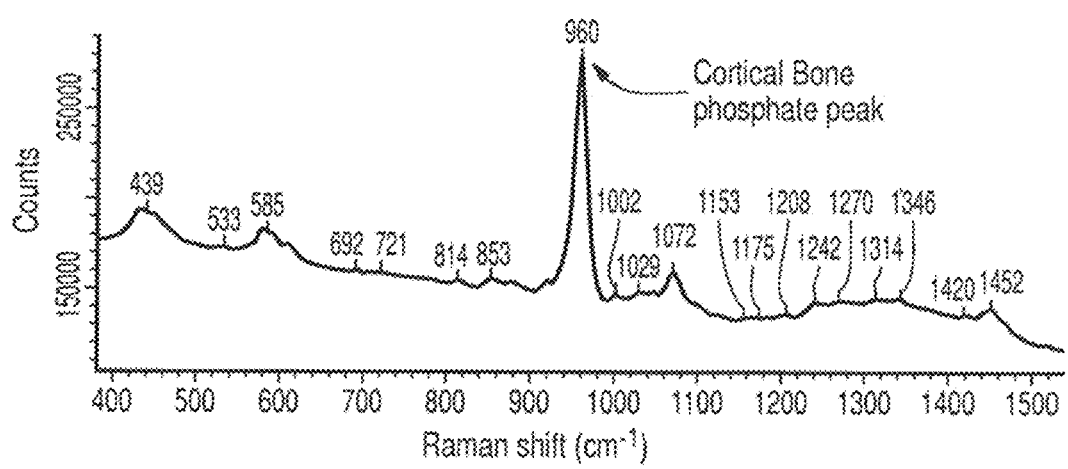
FIG. 11C

MECHANICAL BIOREACTOR

CROSS-REFERENCE

This application is a National Application of International Patent Application No. PCT/EP2016/069700, which was filed on Aug. 19, 2016 and claims the benefit and priority thereto. International Patent Application PCT/EP2016/069700 claims priority and benefit to GB Patent Application No. 1514734.1, which was filed on Aug. 19, 2015.

FIELD OF THE INVENTION

The invention relates to a mechanical bioreactor, i.e. a device for transferring vibrations to cell cultures for the purpose of stimulating various biological processes. The vibrations preferably have a nanoscale amplitude (e.g. less than 100 nm). In particular, the invention is concerned with a bioreactor for stimulating mesenchymal stem cells to induce osteogenesis, i.e. increased expression of osteogenic genes.

BACKGROUND TO THE INVENTION

The increases of life expectancy seen throughout the developed world are a valuable indicator for the state of modern medicine. However, a less quantifiable measure is quality of life during those additional years. The incidence of skeletal injuries along with age related conditions such as osteoporosis and osteoarthritis provide one such metric. Treatments which involve increasing bone density or fracture healing are areas where the regenerative potential of mesenchymal stem cells (MSCs) could prove beneficial [1, 2]. The controlled osteogenesis of MSCs through mechanical means has already been demonstrated through several methods including passive and active means. Passive methods such as altered substrate topography and stiffness provide one mechanism based on altering the adhesion profile [3-7], whilst active methods include exposure to variations of force from external sources [8-13]. Centrifuge, vibration and shear flow have all provided increases in osteogenesis through external modulation of the force experienced by the cell structure. Work by D Ingber has posed a potential description for the highly tuned mechano-sensitive nature of the cytoskeleton when considered as one sensory unit [14, 15]. The varying mechanisms which induce osteogenesis are still being explored and it is now accepted that stimulating cells on the macro and micro scale, using extracellular scaffolds and biomimetic polymers to induce differentiation, is of significant use [16-19]. However, there is now a growing understanding that stimulation and moreover manipulation of the cells at the nano-scale can have a complementary and even greater downstream effect on stem cell differentiation and control [20, 21].

One of the key components which these studies have highlighted is the importance of focal adhesions and integrins as transducers in the osteogenic mechano-transductive process [22, 23]. Altering topography can allow larger more fibrillary focal adhesions to form [24, 25], and the resulting process which drives the osteogenesis of MSCs can include focal adhesion kinase (FAK) signaling. This biological sensory cascade can subsequently be augmented through the mitogen activated protein kinase (MAPK) pathway (including extracellular signal regulated kinase (ERK), and activate Runt-related transcription factor 2 (RUNX2) and osterix. These transcription factors are linked with osteogenic differentiation, along with the genes osteocalcin (OCN), osteonectin (ONN), alkaline phosphatase (ALP) [26-28].

The use of vibration as a mechano-transductive stimulus has been explored with varied vibrational parameters [29-31]. Vibration of periodontal ligament stem cells at 50 Hz (sine wave) with peak acceleration of 3 g showed increased markers of osteogenesis [32] whilst another study of adipose stem cells stimulated using 50 and 100 Hz square waves with accelerations of 3 g showed increased levels of ALP activity and mineral deposition, however not at the same level produced by osteogenic media [33]. Although interesting, neither study mentions the vibration amplitude used. If the focal adhesion complex is important to producing osteogenesis then nanometer sized amplitudes, aimed at the length scale of the integrin complex could find increased stimulation of focal adhesion related signaling.

The use of piezoelectric actuators to produce vibrations of nanometer amplitude has now become a focus for research [21, 34, 35]. Curtis et al. and Nikukar et al. showed that endothelial cells and MSCs are sensitive to amplitudes of tens of nanometers. The use of single actuator, single petri dish devices showed the ability to produce accurate vertical vibration over the entire growth surface. The result of these studies have shown that nanovibration of endothelial cells at low frequencies (1-10 Hz) indicates that protein expression and gene expression linked with an increasing endothelial phenotype are up regulated. In addition experiments incorporating white noise or frequency sweeps show the importance of a coherent signal in producing the biological response. The stimulation of MSCs at higher frequencies (500-1000 Hz), also utilizing nano vibration, have shown the osteogenesis of MSCs. An expansion of this study by Pemberton, Childs et al. up to 5000 Hz used in tandem with nano-topography shows that the two stimuli are not additive with vibration alone producing greater up-regulation of osteogenesis. A comparison of 1, 3 and 5000 Hz also shows that little extra up-regulation of the previous markers is shown above 1000 Hz [36].

SUMMARY OF THE INVENTION

At its most general, the present invention provides a bioreactor that is configured to transmit uniform vibrations across a relatively large (relative to the amplitude of the vibrations) sample receiving surface. This is an important breakthrough because it allows multiple samples to receive identical nanoscale stimulation, which may enable the process to be significantly scaled up. The invention may be particularly applicable to nanoscale vibration amplitudes, where it is non-trivial to design a device that performs this function consistently, because many materials exhibit natural deformation on a scale that would mask or inhibit transfer of nanoscale vibration energy. The invention therefore presents a level of vibration consistency between samples which is unique and required for biological reproducibility.

The bioreactor of the invention may be used as a platform for the consistent osteogenesis of MSCs in vitro by providing stimuli that are both reproducible and precise. The design of the device is such that vertical vibration is delivered in isolation from other effects such as rotation, shear flow, horizontal vibration or surface wave motion. The production of vertical nanoscale vibration with well-defined amplitude, frequency and waveform enables quantitative analysis of the oscillatory acceleration that cells are exposed to along with an estimate of the peak forces applied. This permits the stimuli to be placed in context with other vibrational and centrifugation studies and will allow the comparison of osteogenesis between waveform frequencies, amplitudes and accelerations.

Thus, according to the present invention, there may be provided a bioreactor for imparting vibrations to stimulate mechano-transductive effects in biological tissue, the bioreactor comprising: a vibration actuator; and a sample receiving plate vibratably coupled to the vibration actuator, wherein the sample receiving plate has a plurality of sample mounting locations, and wherein the sample receiving plate is configured to: provide physical engagement to a sample container at each of the plurality of sample mounting locations, and transmit mechanical vibrations having a substantially uniform amplitude (e.g. nanoscale amplitude) across the plurality of sample mounting locations. In use, the sample receiving plate may therefore be configured to receive a plurality of sample containers, each of which may have a one or a plurality of biological tissue samples that receive substantially the same vibrational stimulation. For example, the biological tissue samples may comprise mesenchymal stem cells (MSCs) which are vibrated to induce osteogenesis although the invention is not limited to this particular use.

The bioreactor may deliver uniform vibrations to both two-dimensional and three-dimensional samples. For example, each sample may comprise a thin layer of MSCs which form bone monolayers following stimulation using the bioreactor of the invention. Alternatively, each sample may comprise a gel (e.g. type I collagen or the like) that has been seeded with MSCs in order to increase bone production in a three-dimensional configuration within the gel.

The bioreactor may comprise an array of vibration actuators vibratably coupled to the sample receiving plate in such a way that vibration is consistent across the receiving plate. The array may comprise a plurality of actuator modules, each module having one or more actuators and being independently couplable to the sample receiving plate. The or each actuator may be engaged with the sample receiving plate in any suitable manner and spatial arrangement to transmit vibrational energy and minimize loss of vibration. For example, the sample receiving plate may be mounted on (e.g. above) the array of vibration actuators. The or each vibration actuator may be adhered to the sample receiving plate to remove any play there between. However the invention need not be limited to this location for the vibration actuators in the array. The purpose of the vibration actuators may be to impart a uniform nanoscale vibration to the sample receiving plate. The location and number of vibration actuators may be selected or optimized for this purpose. For example, the spacing between adjacent vibration actuators may be minimized to ensure a uniform oscillation of a top surface of the sample receiving plate. The location of the vibration actuators may thus be independent of the sample mounting locations. In particular, there is no requirement that a vibration actuator be located at each sample mounting location. The sample receiving plate oscillates as a result of the array of vibration actuators acting in combination, and it is this combined action that is transmitted to each sample container. This configuration differs from an arrangement in which each sample has its own dedicated vibration source. For example with this configuration 13 vibration actuators may equally vibrate two 6-well culture plates (containing 12 samples) or larger plate sizes with 12, 24, 96, 384 and 1536 wells providing expansion of the potential number of samples which are vibrated consistently.

The vibration actuator or the array of vibration actuators may be arranged to oscillate the sample receiving plate at nanoscale amplitudes. Herein the term "nanoscale" may be used to indicate a magnitude of 100 nm or less, preferably 30 nm or less. The term "substantially uniform" may be used to indicate a variation of 20% or less, preferably 10% or less. For example, the present invention can deliver a vibration having an amplitude of 30±3 nm to a plurality of samples on the sample receiving plate.

The array of actuators may be driven by a common signal so that that oscillate at a single frequency. The frequency may be in the range 1 to 5000 Hz, preferably 500 to 1500 Hz. A frequency of 1000 Hz may be particular preferred for inducing osteogenesis in mesenchymal stem cells (MSCs).

The bioreactor may include a base block formed from a rigid material such as aluminum that can provide a secure foundation that resists the influence of external effects. The base block may provide large inertial mass under the actuators in order to assist in directing the piezo expansion away from the base, i.e. normal to the top surface of the sample receiving plate. The array of vibration actuators may be mounted on an upper surface of the base block, whereby the sample receiving plate is vibratable relative to the base block. The array of actuators may be arranged to oscillate the sample receiving plate in a direction normal to the upper surface of the base block.

It may be important to have unbroken physical engagement between the vibration actuators and the sample. This may be achieved by securing the sample container to the sample receiving plate, e.g. using any suitable attachment means, such as strapping, clipping or adhesion. In one embodiment, the sample receiving plate may be magnetically couplable to the sample container. The magnetic coupling can provide unbroken physical engagement in an efficient manner. The sample receiving plate may thus be magnetically sensitive and the sample container may be magnetic or vice versa. The sample receiving plate may have a multilayer construction comprising a rigid lower layer (e.g. of aluminum) and a magnetically sensitive upper layer (e.g. of stainless steel). The sample container may have a magnetic undersurface for engaging the sample receiving plate. The sample container may comprise a plurality of wells for receiving biological tissue samples, whereby the plurality of wells are positioned at the plurality of sample mounting locations when the sample container is mounted on the sample receiving plate.

The magnetic undersurface may be bonded to the rest of the sample container. For example, the magnetic undersurface may comprise a magnetic disk mounted at the base of each of the plurality of wells. These magnets may be secured using a layer of adhesive (e.g. epoxy). Using a layer of adhesive in this way may also improve the physical engagement because it can prevent any air gaps from existing beneath the sample container. Alternatively, magnetic material may be formed integrally with the sample container, e.g. incorporated during injection molding. Preferably, the magnetic material is a Halbach array having a magnetic field directly away from the sample, in order to avoid exposing the cells in the sample to a magnetic field which may alter biological processes itself.

Preferably the bottom of the sample container is flexible to facilitate formation of a unbroken and even adhesive layer. Each actuator in the array of actuators may be adhered to the sample receiving plate in a similar manner.

The bioreactor may include a generator arranged to deliver an oscillating drive signal to each actuator in the array of actuators. Each actuator comprises a piezoelectric element, whereby application of the oscillating drive signal across the piezoelectric element causes an oscillating (i.e. periodic) nanoscale deformation of the actuator.

The actuators may be connected to the generator in series or parallel. The generator may be configured differently depends on the wiring configuration. For example, if the actuators are connected in series, the generator may comprise a voltage source and an oscillator. The voltage source may have an adjustable output voltage for controlling the vibration amplitude of the array of actuators, and the oscillator may be adjustable to vary the frequency of vibration. Alternatively, if the actuators are connected in parallel, the generator may comprise a network amplifier. The network amplifier may have an adjustable amplifier volume for controlling the vibration amplitude of the array of actuators. In practice, the parallel-connected actuators may be driven by any suitable amplifier device arranged to deliver an oscillating drive signal.

The structure for the sample receiving plate and or sample container may be determined using finite element modelling and/or real interferometric experiments. In an embodiment derived using this technique, the sample receiving plate comprises a 6 mm thick lower plate made of aluminum bonded (using epoxy) across its whole surface to a 6 mm thick layer of stainless steel. This structure may provide a rigidity vs weight combination that avoids unwanted resonance effects and minimizes variations in the vibration amplitude over the surface, whilst also providing a magnetically sensitive top surface.

1. A bioreactor for imparting nanoscale vibrations to stimulate mechano-transductive effects in biological tissue, the bioreactor comprising: a vibration actuator; and a sample receiving plate vibratably coupled to the vibration actuator, wherein the vibration actuator is arranged to vertically oscillate the sample receiving plate at nanoscale amplitudes, wherein the sample receiving plate has a plurality of sample mounting locations, and wherein the sample receiving plate is configured to: provide physical engagement to a sample container at each of the plurality of sample mounting locations, and transmit mechanical vertical vibrations having a substantially uniform nanoscale amplitude across the plurality of sample mounting locations.

2. A bioreactor according to claim 1 comprising an array of vibration actuators vibratably coupled to the sample receiving plate.

3. A bioreactor according to claim 2, wherein the sample receiving plate is mounted on the array of vibration actuators.

4. A bioreactor according to any preceding claim, wherein the or each vibration actuator is adhered to the sample receiving plate.

5. A bioreactor according to claim 1 or 2, wherein the or each vibration actuator is part of a respective sample container.

6. A bioreactor according to claim 2 or 3 including a base block, wherein the array of vibration actuators is mounted on an upper surface of the base block, whereby the sample receiving plate is vibratable relative to the base block.

7. A bioreactor according to claim 6, wherein the array of actuators is arranged to oscillate the sample receiving plate in a direction normal to the upper surface of the base block.

8. A bioreactor according to any preceding claim, wherein the sample receiving plate is secured in unbroken physical contact with the sample container.

9. A bioreactor according to any preceding claim, wherein the sample receiving plate is magnetically couplable to the sample container.

10. A bioreactor according to claim 9, wherein the sample receiving plate has a multilayer construction comprising a rigid lower layer and a magnetically sensitive upper layer.

11. A bioreactor according to claim 10, wherein the upper layer is stainless steel.

12. A bioreactor according to claim 10 or 11, wherein the lower layer is aluminum.

13. A bioreactor according to any one of claims 9 to 12 including a sample container having a plurality of wells for receiving biological tissue samples, wherein the sample container has a magnetic undersurface for engaging the sample receiving plate, whereby the plurality of wells are positioned at the plurality of sample mounting locations.

14. A bioreactor according to claim 13, wherein the magnetic undersurface comprises a magnetic disk mounted at the base of each of the plurality of wells.

15. A bioreactor according to any preceding claim including a generator arranged to deliver an oscillating drive signal to the or each vibration actuator.

16. A bioreactor according to claim 15, wherein the or each vibration actuator comprises a piezoelectric element, whereby application of the oscillating drive signal across the piezoelectric element causes periodic deformation of the actuator.

17. A bioreactor according to claim 15 or 16, wherein the array of vibration actuators consists of a plurality of actuators connected in series with the generator.

18. A bioreactor according to claim 17, wherein the generator comprises a voltage source and an oscillator.

19. A bioreactor according to claim 18, wherein the voltage source has an adjustable output voltage for controlling the vibration amplitude of the array of actuators.

20. A bioreactor according to claim 15 or 16, wherein the array of vibration actuators consists of a plurality of actuators connected to the generator in parallel.

21. A bioreactor according to claim 20, wherein the generator comprises an amplifier.

22. A bioreactor according to claim 21, wherein the amplifier has an adjustable amplifier volume for controlling the vibration amplitude of the array of vibration actuators.

BRIEF DESCRIPTION OF THE DRAWINGS

Examples of the invention are now discussed in detail with reference to the accompanying drawings, in which:

FIG. 11A is a photograph of three collagen gels used to demonstrate the applicability of the invention to three-dimensional samples;

FIG. 11B is a graph showing intensity measurements from the gels in FIG. 11A;

FIG. 11C shows Raman spectra of bone;

DETAILED DESCRIPTION; FURTHER OPTIONS AND PREFERENCES

The description below explains how finite element modelling can be used to design and optimize the construction of a bioreactor, which can minimize amplitude uncertainty arising from resonances or substrate deformations. These factors are important when using nanoscale amplitudes as consistent vibration amplitude ensures that all cells on the bioreactor experience the same levels of acceleration. Since previous setups have shown stimulation at 35 nm and 1000 Hz to produce a strong osteogenic effect, the embodiment of the invention discussed below was aimed at encompassing this within its working range [21]. During construction, laser interferometry was utilized to characterize the vibrational output from the device at several stages. Finally the bioreactor was characterized biologically, involving the genetic/transcriptomic and proteomic assessment of MSC's exposed to nano vibrational stimuli in terms of osteogenesis.

The following discussion presents firstly the design, construction and validation of a bioreactor that is an embodiment of the invention and capable of inducing osteogenesis within MSCs. Through the use of finite element modelling and interferometric measurement, a bioreactor design capable of producing nanoscale vibrations up to 4000 Hz is disclosed. The embodiment is shown to be capable of providing consistent vibrational amplitudes (up to 190 nm at high frequency) across a 6 and 24-well plate. This enables parameter setting biological experiments to be carried out to find an optimum osteogenic condition for the bioreactor.

The discussion goes on to demonstrate that exposure of MSCs to stimulation (22 nm amplitude at 1000 Hz) increases expression of the osteogenic genes (osteocalcin, alkaline phosphatase, osteonectin and the transcription factor osterix) as measured via a quantitative real time polymerase chain reaction (PCR). Moreover, the osteogenic transcription data is shown to mirror closely an increase in key genes (FAK, ERK1&2, MAP2K1&2) related to the MEK/MAPK pathway, which has proved to be a pivotal instigator of piezo-related osteogenesis. Immunostaining of the osteogenic related transcription factors RUNX2, in its activated or phosphorylated form, also demonstrates that this effect extending downstream to the protein level. The accuracy of stimulation presented here allows fine-tuning of mechanically stimulated osteogenesis in a manner previously unachievable.

Figure 1:
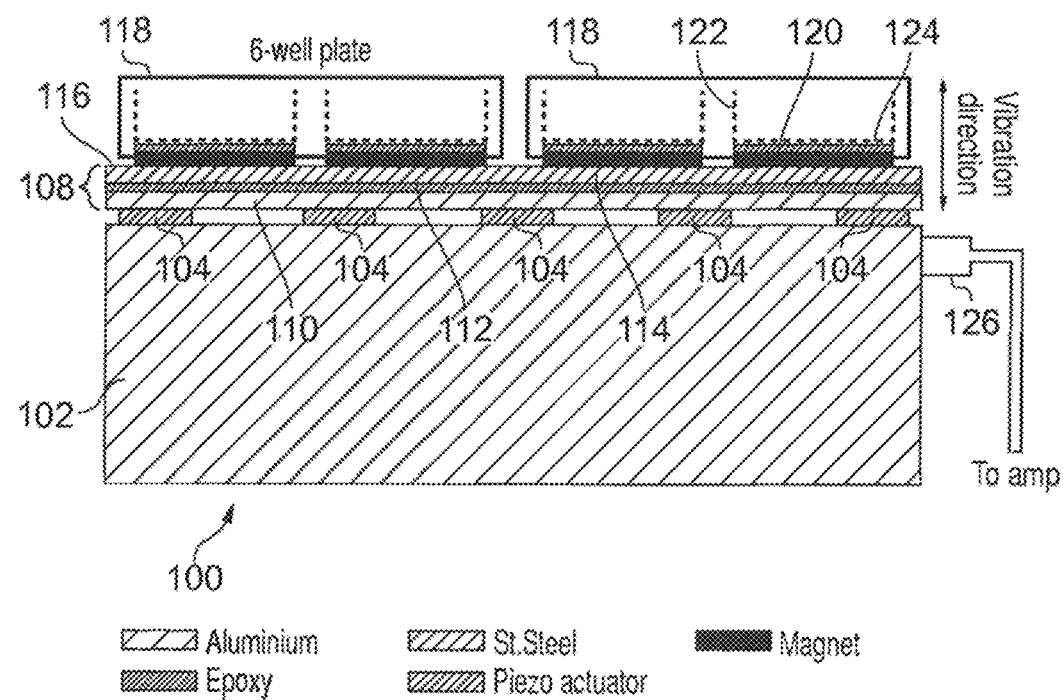
FIG. 1 is a schematic cross-sectional view of a vibration apparatus that is an embodiment of the invention.
Figure 2:
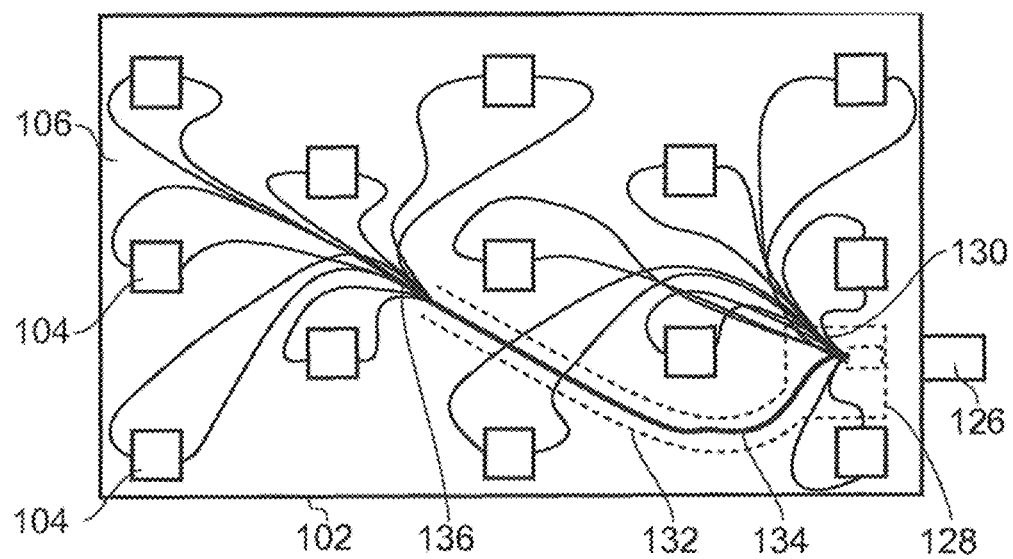
FIG. 2 is a plan view of an actuator layout suitable for use in the vibration apparatus of FIG. 1.

FIG. 1 shows a schematic cross-sectional view through a bioreactor 100 that is an embodiment of the invention. The bioreactor 100 comprises a rigid base block 102, e.g. made from aluminum, having an array of vibratable actuators 104 mounted thereon. In this embodiment, there are thirteen actuators 104 distributed over an upper surface 106 of the base block 102 as shown in FIG. 2. Each actuator comprises a piezoelectric element, i.e. a component that can physically deform upon application of an electric field across it. For example, the actuators may be piezo-actuators PL088.30 from Physik Instrumente (Karlsruhe, Germany), which has a low profile and relatively large attachment area (i.e. 0.2 cm height with 1 cm² attachment area) to increase adhesive bonding to the top and bottom surfaces whilst minimizing the risk of detachment due to shear forces. Each actuator 104 is secured to base block 102 so that the vibrational movement of the actuator occurs relative to the base block in a direction normal to the top surface 106 thereof. Each actuator may be secured by a suitable adhesive, e.g. epoxy (not shown).

A top plate 108 is mounted above (over) the array of actuators. The top plate is a rigid body, and may be made from the same material as the base block, e.g. aluminum. The top plate is secured to the array of actuators 104 so that the vibrational movement of the actuators is transferred to movement of the top plate. The top plate may be secured to one or more or all of the actuators using a suitable adhesive (e.g. epoxy).

The top plate is dimensioned to avoid the create of regions of resonance when the actuators are vibrating. In this embodiment, the top plate is a multi-layered structure comprising a 6 mm thick lower layer 110 of aluminum bonded via epoxy intermediate layer 112 to 6 mm thick upper layer 114 of magnetically-sensitive stainless steel (e.g. grade 420 stainless steel). The lower layer 110 is secured (i.e. bonded) to the array of actuators 104. Using two materials in the top plate 108 permits allows the minimization of weight (which has an effect on piezo mechanics) whilst minimizing deformation at the nanoscale and allowing magnetic attachment, as discussed below.

The upper layer 114 present a top surface 116 of the device, which acts as a platform for receiving one of more plates 118, each of which contain a plurality of wells for holding samples to be vibrated. In this embodiment, the top surface 116 is dimensioned to permit attachment of two 6-well plates 118, each having dimensions of 130×178 mm. It is important for the plates 118 to be in intimate contact with the top surface so that the vibrations are passed in a uniform manner. In this embodiment, the plates 118 are magnetically attached to the top surface 118. In this example the magnetic attachment is achieved by providing a plurality of ferrite magnets 120, each of which is attached to the base of a respective well 122 in one of the plates 118 via a layer 124 of adhesive. The base of each well and/or the base of the sample container received in each well may be flexible to facilitate unbroken physical contact between the magnet and the top surface of the sample receiving plate. In this case, the layer 124 of adhesive may not be required. There are therefore twelve magnets in this example. Preferably a single magnet is provided under each well or under each well plate. The magnets may be oblong (to match the shape or well plate) or disc-shaped (to match the shape of a well). For example, each magnet may be a disc having a 30 mm diameter and 3 mm thickness such as those manufactured by Magnet Expert (Tuxford, UK). The quoted magnetic flux at the surface of these magnets is 700 gauss (0.07 T) which as a static magnetic field is not thought to be high enough to alter cellular function [42]. However these magnets, being Halbach arrays, are only magnetic on the side facing the bioreactor and away from the cell culture therefore any stray magnetic fields will be far smaller.

The magnets 120 serve three purposes. Firstly they ensure adequate transfer of vibration amplitude to the 6-well plates. Secondly they enable consistent transfer of vibration amplitude to each well on the plate. Thirdly they permit easy removal of the plate at the end of the treatment.

The use of adhesive (e.g. epoxy) to bond the 6-well plate 118 to its magnets 120 ensures that each well is in complete physical contact with the bioreactor surface. The adhesive can fill any air gaps which could otherwise occur due to manufacturing variance between individual plates.

The base block 102 has a connector port 126 on a side surface thereof for receiving a stimulation signal to be conveyed to each actuator 104. As discussed below, the stimulation signal is provided by a generator that has a different configuration depending on whether the actuators are connected in series or parallel. Where the actuators are connected in series, the generator comprises a high voltage driver (e.g. Model ENV 150, Piezosystemjena, Jena, Germany), which is capable of providing 160 $V_{pk-pk}$. In this case the generator includes an oscillator arranged to modulate the output of the high voltage driver, e.g. as a sine wave. The oscillator may be a signal generator such as Model 33210A, from Agilent (Santa Clara, Calif.). If the actuators are wired in parallel, the generator may comprise a network amplifier (Sneaky OS, Linn Products, Glasgow, UK) to provide a high power output. The signal waveform in this case may be provided by a networked computer installed with Linn Kinsky software. For example, FLAC waveform files produced in Audacity 2.0.5 can be sent through the network amplifier. The volume of the amplifier output is controlled through Kinsky on a scale of 0-100 which was used for amplitude calibration during interferometry as discussed below.

FIG. 2 shows a plan view of the upper surface 106 of the base block 102 which shows how the actuators 104 are distributed in this embodiment. The actuators are evenly distributed on the upper surface 106. The distribution may be seen as a series of nested oblongs. In this example, the nested oblongs comprise a first set of eight actuators around the edge of the upper surface, a second set of four actuators within the first set, and a final set comprising a single actuator in the middle of the upper surface. The number of nested oblongs and the number of actuators in each oblong may be selected based on the geometry of the upper surface, e.g. in conjunction with the modelling discussed below.

FIG. 2 also shows how the voltage signal from the connector port 126 is delivered to the actuators 104. A recess 128 is machined into the upper surface in a location without an actuator. A first set of wired connections 130 extends from the recess 128 to a group of actuators located closer to the connector port 126. A recessed channel 132 carries a cable 134 from the recess 128 further across the upper surface, from where a second set of wired connections 136 extends from an end of the recessed channel 132 to the remaining actuators located further from the connector port 126.

Figure 3:
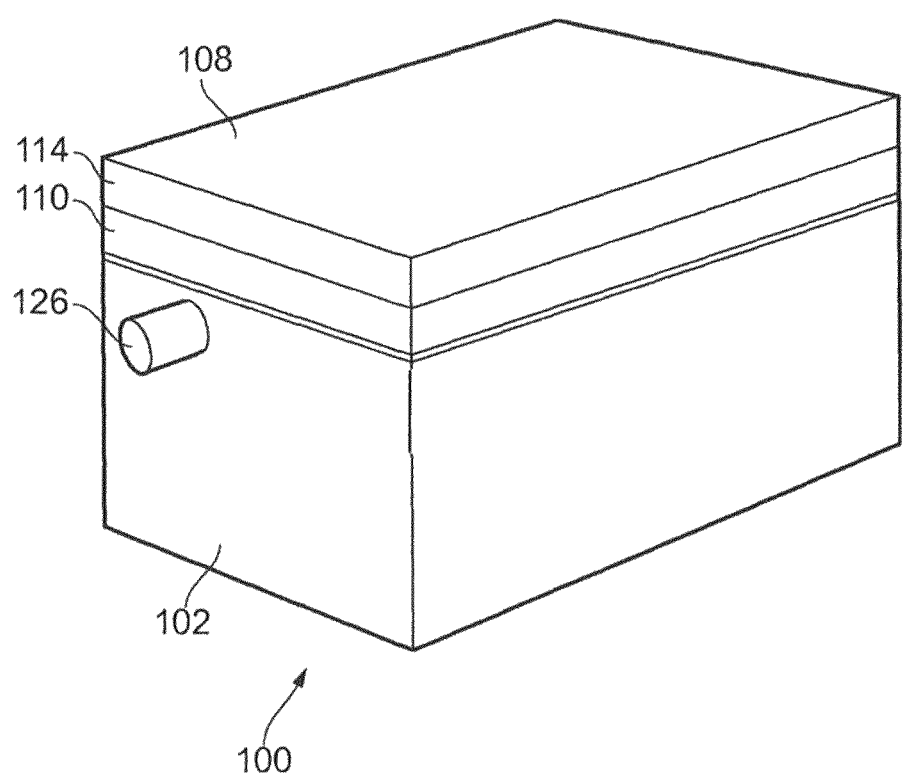
FIG. 3 is a schematic perspective of the vibration apparatus of FIG. 1.

The thickness of the epoxy layers and actuators is exaggerated in FIG. 1 for the purposes of explanation. FIG. 3 shows a perspective view of the bioreactor before the plates 118 are mounted thereon which shows the relative dimensions more accurately.

An additional advantage of the bioreactor described above is that its geometry enables easy maintenance of a sterile environment for long term biological cultures, because the entire bioreactor and/or the 6-well plates is small enough to be easily introduced to a laminar flow fume hood for addition of media, feeding of cells (growth of skeletal tissue) or carrying out experiments in a controlled sterilized environment.

Aside from the structural resonances of the bioreactor, the piezo actuators have a resonant frequency associated with them ($f_0$). For a given mass load (M) the actual resonant frequency ($f_0'$) varies as Equation (1) [37]:

$$f_0' = f_0 \sqrt{\frac{m/3}{m/3 + M}} \qquad (1)$$

where m is the actuator mass. The frequency of this resonance is important because vibration amplitude increases at this frequency. For example, assuming a load (M) of 189 g per actuator and an actuator mass (m) of 0.2 g, equation (1) provides an estimated resonance of 31.4 kHz which is beyond the limits of the amplifiers used.

FIGS. 4A to 4F show some results of finite element modelling utilized to determine resonant frequencies (using modal analysis) and deformation (using harmonic response analysis) of components due to vibration. ANSYS simulation software was used to perform the modelling.

Figure 4:
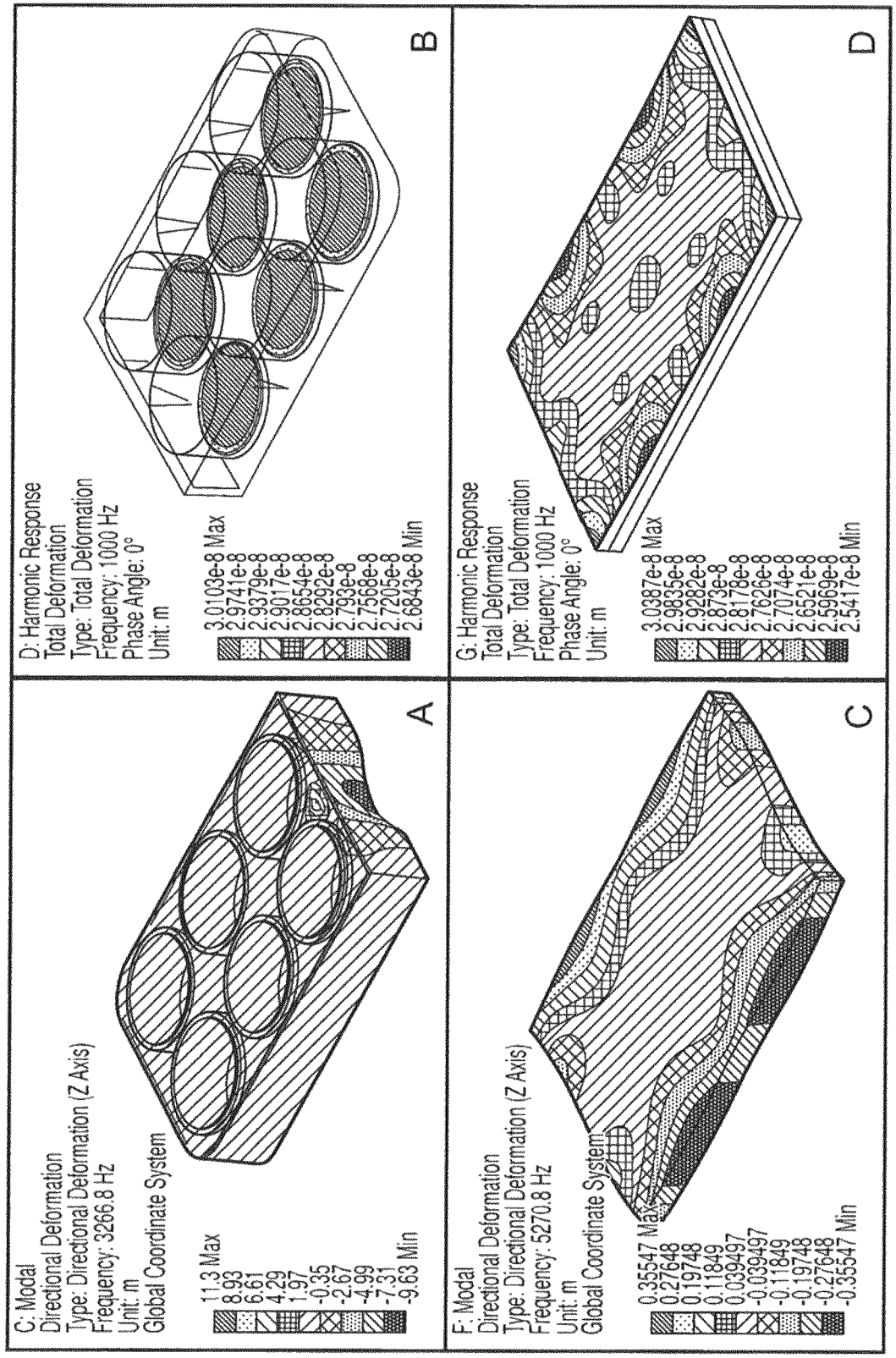
FIG. 4A shows a modal analysis of a simulated 6-well plate at the lowest resonant frequency.
FIG. 4B shows a harmonic response analysis of the simulated 6-well plate at 1000 Hz (30 nm amplitude)
FIG. 4C shows a modal analysis of a preferred top plate configuration at lowest resonant frequency.
FIG. 4D shows a harmonic response analysis of the preferred top plate configuration at 1000 Hz (30 nm amplitude)
FIG. 4E shows a frequency response of a 6-well plate showing maximum and minimum amplitudes.
FIG. 4F shows a frequency response of composite top plate showing maximum and minimum amplitudes.
Figure 4:
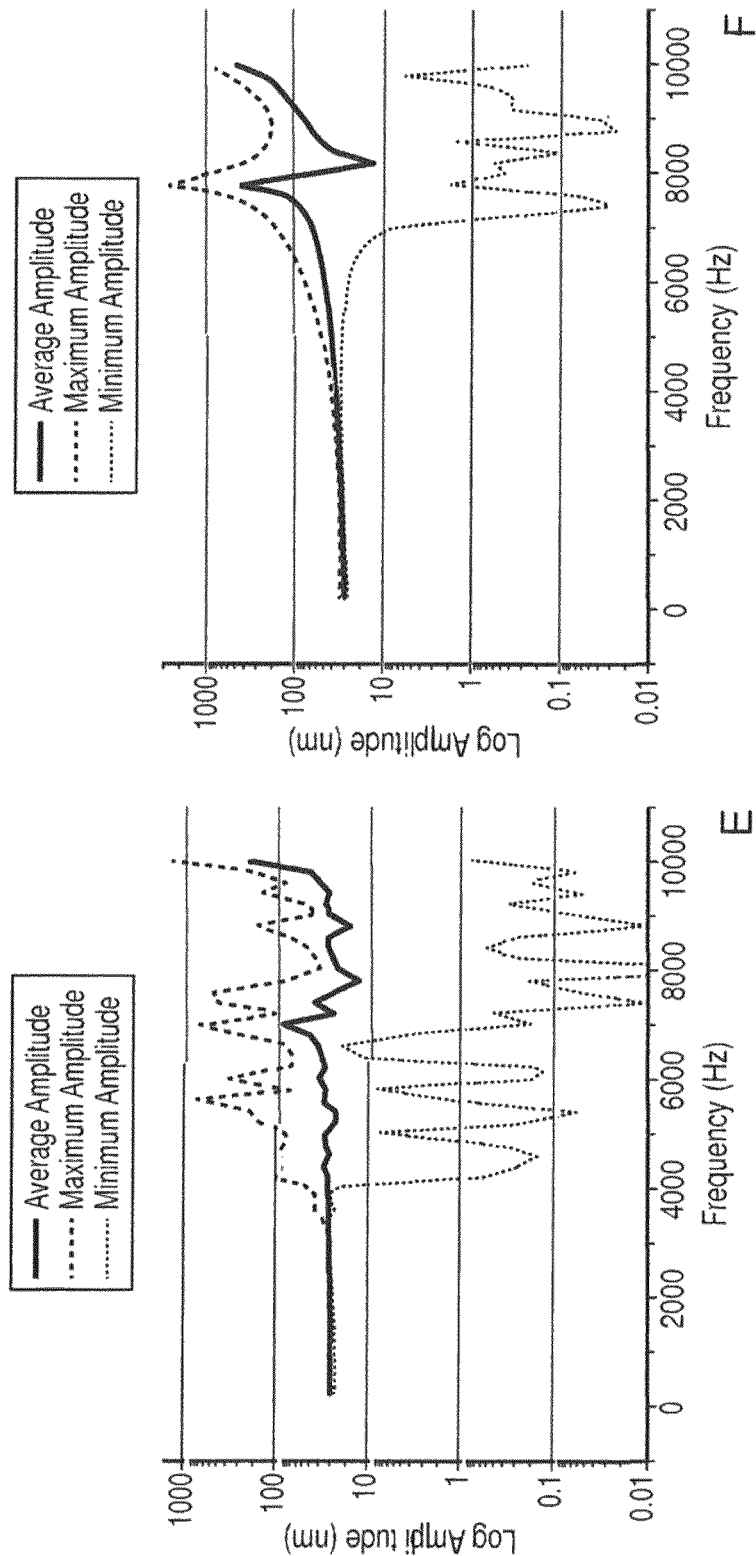

FIG. 4A shows a modal analysis of a modelled 6-well plate, which is shown to produce a lowest resonance value of 3267 Hz. Although there is a resonance occurring at this frequency, the mode shape does not deform the base of the six wells so would not impact stimulation intensity over the growth area. FIG. 4B shows a harmonic response analysis which confirms that the magnetic attachment across the six wells should maintain amplitude accuracy across the growth surfaces. FIG. 4E demonstrates that amplitude accuracy can be maintained within 3.3 nm (11%) for frequencies up to 3600 Hz.

FIGS. 4C and 4D shows the results of modelling that was perform to determine the desired materials and thickness for the top plate of the bioreactor. Several material combinations were modelled with the lowest resonance noted in each case via modal analysis. Harmonic response analysis performed at 1000 Hz with 30 nm amplitude provided a value for the spread of amplitudes across the top plate due to deformation. Table 1 shows the results of this modelling for various top plate constructions.

TABLE 1

Collation of data produced from modal and harmonic response analysis in ANSYS. For each top plate configuration a value for lowest resonance is obtained along with the spread of amplitudes when vibrated at 1000 Hz with 30 nm amplitude.

| Layer 1 | Layer 2 | Layer 3 | No. of Actuators | 1st Resonance [Hz] | Amp. range [nm] |
|---------|---------|---------|------------------|--------------------|-----------------|
| 6 mm Al | 0.6 mm St. Steel | | 5 | 1953.7 | 57 |
| 6 mm Al | 6 mm Al | 0.6 mm St. Steel | 5 | 2879.7 | 40 |
| 6 mm Al | 0.6 mm St. Steel | | 13 | 6637.8 | 7 |
| 6 mm Al | 6 mm St. Steel | | 13 | 5270.8 | 5 |
| 6 mm SiC | 0.6 mm St. Steel | | 13 | 9149.9 | 2 |

A preferred top plate composition comprises a 6 mm thick aluminum lower layer and a 6 mm thick magnetically responsive stainless steel upper layer bonded to the lower layer with a 0.1 mm thick layer of epoxy. These parameters provide rigidity to minimize deformation at a nanometer scale and maximize resonant frequencies whilst keeping the load on the actuators to a minimum. Modal analysis produced a lowest resonance value for this choice of materials of 5270.8 Hz.

Other materials may be used to provide the same or similar benefits. For example, one of the modelled structures had a lower layer made from SiC rather than aluminum. This structure provided a slight benefit in terms of amplitude consistency over aluminum.

The number of actuator attachment points was also varied in the simulated model as initial tests had shown reduced vibration of the top plate if the gap between actuators was too great. FIG. 4F shows the amplitude variation with frequency for the configuration of thirteen actuators shown in FIG. 2. This configuration produced amplitude consistency of 5 nm (17%) based on 30 nm vibration at 1000 Hz.

Actuator wiring is also an important factor which can affect the amplifier requirements for the piezo array. The network of thirteen actuators shown in FIG. 2 are connected by parallel wiring (PW). However, it is also possible to connect them using series wiring (SW). The choice of connection alters the effective capacitance of the network. The maximum current $I_{Max}$ required at a vibration frequency f can be estimated by Equation (2).

$$I_{Max} \approx f \pi C_{Total} U_{pk-pk} \qquad (2)$$

The effective capacitance $C_{Total}$ of the thirteen actuator array is calculated differently depending on wiring choice with values of 85 and 14,300 nF for SW and PW respectively. Accordingly, the peak to peak voltage $U_{pk-pk}$ required to produce a desired vibration amplitude depends on the wiring configuration. Based on the nominal voltage quoted for the chosen piezoelectric actuators used in the embodiment discussed above, the total voltage required to produce 30 nm vibration amplitudes would be 35 and 2.7 $V_{pk-pk}$ for SW and PW respectively assuming no loss of amplitude due to epoxy bonding.

For an amplitude of 30 nm at 5000 Hz this gives peak current and voltage requirements of 47 mA and 35 $V_{pk-pk}$ respectively when connected via SW. For PW the same requirements are 606 mA and 2.7 $V_{pk-pk}$. These requirements are such that different amplification methods are required depending on the wiring setup used.

A high voltage amplifier and a high power network amplifier were utilized to test the SW and PW configurations respectively. Both amplitude consistency and maximum amplitude were found to be higher with the PW configuration as shown in the interferometric measurements discussed below.

Figure 5:
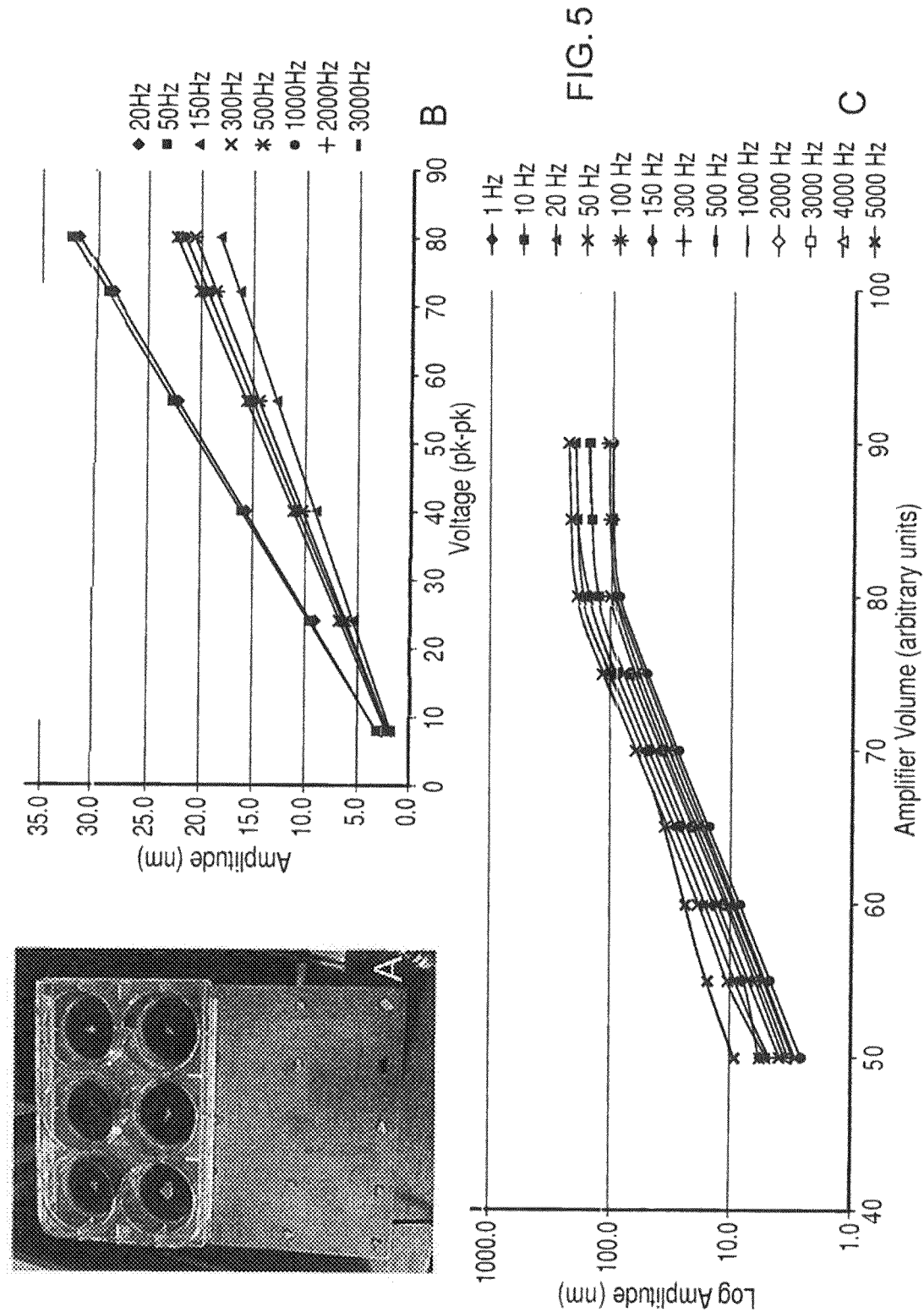
FIG. 5A is a plan view of vibration apparatus according to an embodiment of the invention during interferometric measurement.
FIG. 5B shows calibration data for a series wired bioreactor (including magnet attached 6-well plate)
FIG. 5C shows calibration data for a parallel wired bioreactor (including magnet attached 6 well plate)
FIG. 5D shows interferometric measurement data from the bioreactor top plate when wired in parallel.
FIG. 5E shows a comparison of frequency response for parallel wired (PW) piezos before attachment of top plate and 6-well plates attached to the surface of either a parallel or series wired (SW) bioreactor receiving an amplifier volume of 70 and voltage of 80 $V_{pk-pk}$ respectively.
Figure 5:
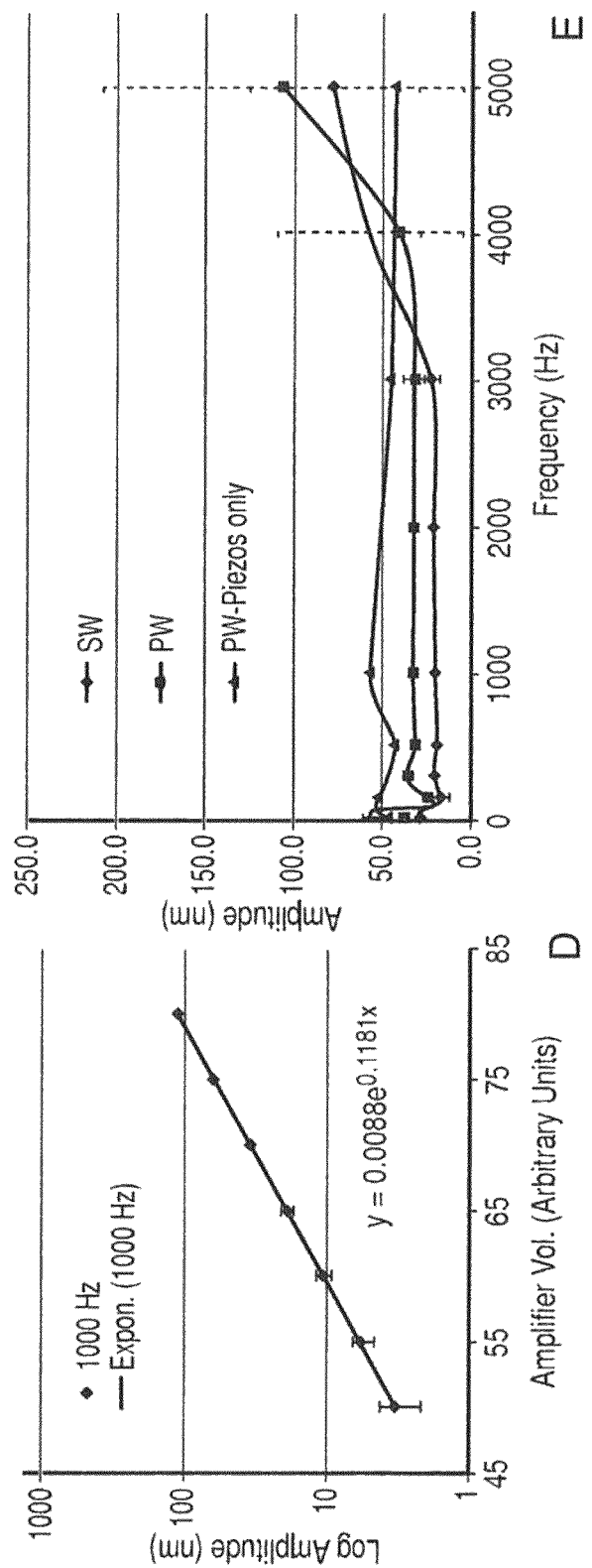

FIG. 5 presents the results of laser interferometry measurements used to provide confirmatory data for the finite element modelling. Measurement of the actuator amplitudes without a top plate attached gave an average amplitude for the SW configuration of 24.7 nm with an accuracy of 8.3% between actuators (1000 Hz, 80 $V_{pk-pk}$). In contrast, the PW configuration produced an amplitude of 207.4 nm with 9.5% accuracy across the actuators (1000 Hz, amplifier volume–100). Increased levels of accuracy (7.5%) were found with lower amplifier volume (60). Similar measurements were performed after attachment of the top plate. Both wiring configurations exhibited a reduced vibration amplitude when the top plate was in place, but the PW configuration amplitude was still far higher than the amplitude produced with the SW configuration.

FIG. 5A shows a plan view of the experimental setup, in which 25 silica fragments are mounted in a regular array on the top plate to provide a surface for reflection of the interferometer laser in the absence of a 6-well plate. When a 6-well plate is present, a silica fragment is provided in the base of each well. Amplitude measurement of the top plates gave motion of 28.2 and 34.6 nm with an amplitude consistency of 11.2% and 9.3% across 25 measurement points using the SW configuration and PW configuration respectively.

FIG. 5E shows a comparison between the wiring layouts. The PW configuration measurements were taken at an amplifier volume of 70. The error bars in FIG. 5E signify standard deviation. FIG. 5D shows further data collected at this stage which relating the output amplitudes to amplifier volume. Calibration of the top surface was carried out at 1000 Hz.

When the 6-well plates were attached to the top plate, the measurement indicated a further reduction in amplitude, which is expected because another layer has been added between the actuators and the measurement point. However, amplitude consistency across multiple wells was shown to be consistent with an accuracy of 21.2% and 8% for SW and PW respectively in the range of 0-3000 Hz. As shown in FIG. 5E, at 4-5 kHz the accuracy of the vibration diminishes and average amplitude appears to increase towards a resonance.

Once amplitude consistency is established across the base of the wells, which provide a growth surface of the bioreactor, calibration data for input voltage (for the SW configuration) or input volume (for the PW configuration) was collected. FIG. 5B shows the input voltage calibration data. Frequencies of 4 and 5 kHz are omitted from this graph due to their magnitude being far higher than the range presented. FIG. 5C shows the input volume calibration data. This data may be used to provide the basis from which to choose vibration amplitude for subsequent cell studies.

Measurement was also taken using 24-well plates to determine if their use would achieve the same level of vibration consistency. The plates, which were again attached with 6 magnets, were measured at the four corner wells and four center wells over two plates whilst being vibrated on the SW bioreactor with 80 $V_{pk-pk}$ (Table 2). With the exception of 4000 Hz, each vibration amplitude was found to be larger at the corners reducing overall accuracy and reproducibility of results. These issues can be avoided by improving the spatial relationship between the magnets and the wells, e.g. by using 24 small magnets (one per well) or 6 square magnets (one per well plate).

TABLE 2

24-well plate interferometry data. Average from 16 wells (2 plates) is shown along with the average over 8 corner and 8 center wells. Standard deviations σ are shown in nanometers and as a percentage of the measured amplitudes.

| Frequency [Hz] | Average [nm] | σ [nm] | σ [%] | Corners [nm] | σ [nm] | Centre [nm] | σ [nm] |
|---|---|---|---|---|---|---|---|
| 1000 | 18.1 | 13.4 | 74.3 | 20.0 | 18.4 | 16.2 | 6.2 |
| 2000 | 12.2 | 8.5 | 69.5 | 17.6 | 8.6 | 6.7 | 3.3 |
| 3000 | 11.9 | 9.1 | 76.4 | 13.4 | 10.2 | 10.4 | 8.3 |
| 4000 | 13.2 | 12.4 | 94.2 | 9.7 | 9.9 | 16.6 | 14.3 |

As can be seen from the calibration data in FIGS. 5B and 5C, vibration amplitude increases linearly with input voltage for SW and exponentially with input volume for PW due to the amplifier volume scale being non linear. As shown in the previous amplitude consistency check, accuracy of vibration drops drastically as frequency increases above 3 kHz. The calibration data shows that amplitudes at these higher frequencies varied between measurements by 90 and 55% for SW and PW respectively. Another finding is that the point where the amplitude plateaus is usually accompanied by harmonics of the stimulation frequency appearing on the frequency spectrum.

With precise values measured for the vibration amplitude at each frequency and input voltage/volume it is possible to provide values for the acceleration and force involved in the stimulation. A sinusoidal vibration allows straightforward calculation of peak acceleration via Equation (3) using amplitude $A_0$ and frequency f [35].

$$\text{Acceleration}_{peak} A_0 (2\pi f)^2 \qquad (3)$$

By utilizing Newton's second law and calculating the mass of media directly above one cell (cell surface area multiplied by media height and by media density) it is also possible to estimate the force exerted during peak 25 acceleration by individual cells.

Interferometric data showing the amplitude accuracy of the bioreactor can be used to demonstrate the wide range of acceleration which can be produced by the bioreactor. This range is shown for a frequencies 0-500 Hz in FIG. 6A and for frequencies of 500-5000 Hz in FIG. 6B based on a PW configuration bioreactor powered by amplifier volume of 70. Error bars represent the standard deviation of interferometric measurements.

The following section describes experiments which demonstrate the capability of the bioreactor described above to stimulate osteogenesis. Using a qRT-PCR technique, mRNA from unstimulated controls is used to assess the prevalence of an increase in osteogenic related genes through vibration of samples using the bioreactor. In order to maintain consistency through the experiment and reduce variability the controls were also cultured with magnets beneath the plates, but were not stimulated by nanoscale vibration. It was observed that all four genes assessed (osterix, alkaline phosphatease, osteocalcin and osteonectin) showed an increase compared with the control, with the gene ALPL encoding for alkaline phosphatease and the BGLAP gene coding for osteocalcin showing significance relative to the controls.

Figure 7:
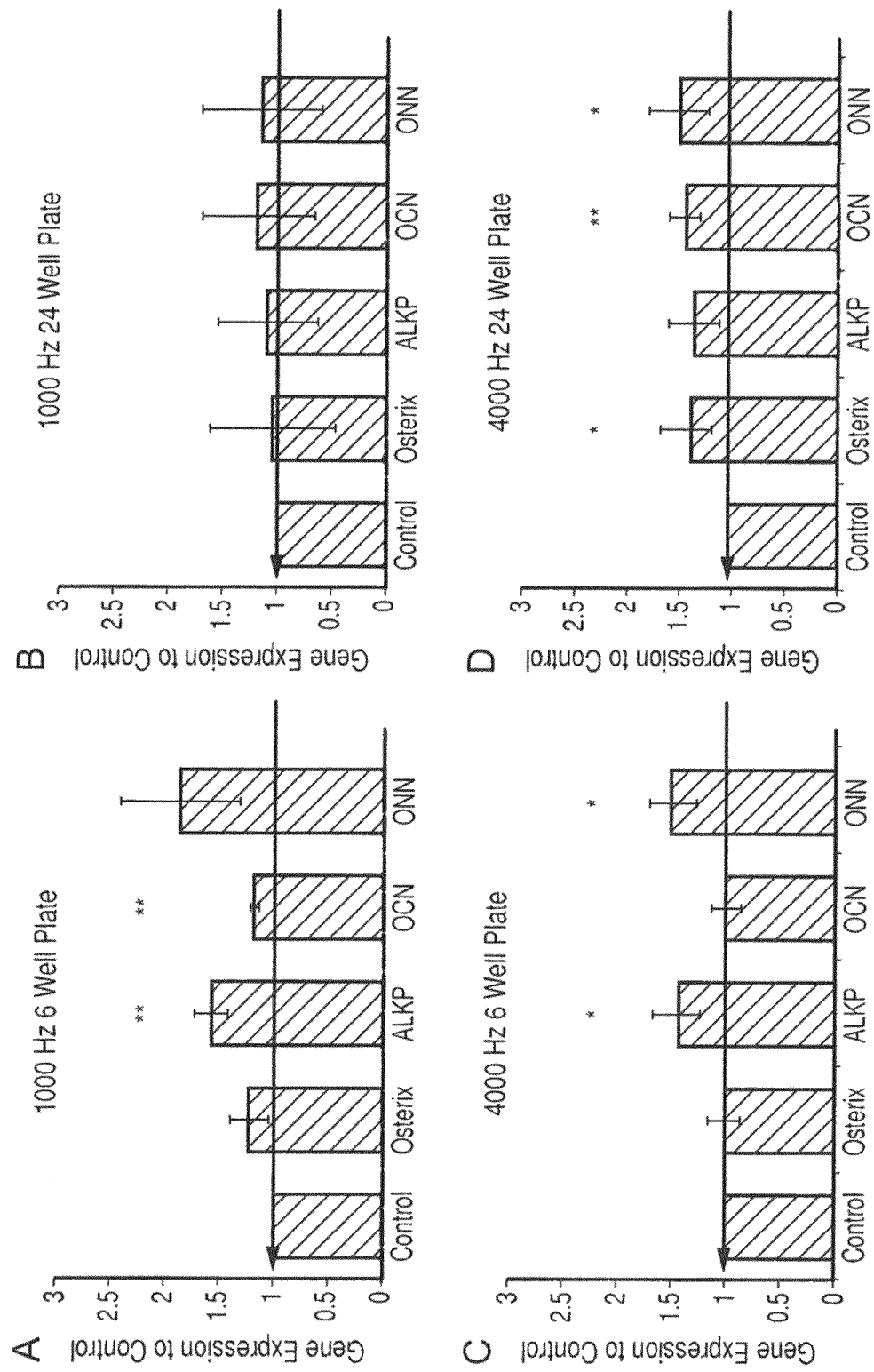
FIGS. 7A to 7D show transcriptional analysis results for a quantitative real time polymerase chain reaction (qRT-PCR) for mRNA gene expression.

FIG. 7 shows the results following stimulation of MSCs on the vibrational bioreactor described above for 8 days. FIG. 7A shows the results from vibrating the MSCs at a frequency of 1000 Hz in a 6-well plate. FIG. 7B shows the results from vibrating the MSCs at 1000 Hz in a 24 well plate. FIG. 7C shows the results from vibrating the MSCs at 4000 Hz in a 6-well plate. FIG. 7D shows the results from vibrating the MSCs at 4000 Hz in a 24 well plate. The subsequent gene expression of osterix, alkaline phosphatase, osteocalcin and osteonection were assessed relative to an unstimulated control. All experiments were carried out at an amplitude of 5 V with a 22 nm vertical displacement. The results were obtained using a 20 paired t-test, and show the average of three measurements, with the standard deviation indicated by error bars. The standard deviation for the results marked * was <0.05 and for the results marked ** was <0.01.

FIGS. 7A and 7D, i.e. 1000 Hz vibration with a 6-well 25 plate and 4000 Hz vibration with a 24 well plate respectively, objectively provide the best results. However, FIG. 7A appears to be the most in line with the up-regulation of genes related to MEK/MAPK (see FIG. 8A) and hence is likely to provide the most reproducible biological result. Osteocalcin is secreted solely by osteoblasts, which supports the prevalence of stem cell differentiation using this vibrational bioreactor. On the contrary, the MSC cultured in a 24 well plate with a 1000 Hz vibration, showed almost no up regulation of the same osteogenic genes and 4000 Hz with the 6-well plate provided a less consistent stimulation of these genes.

Figure 8:
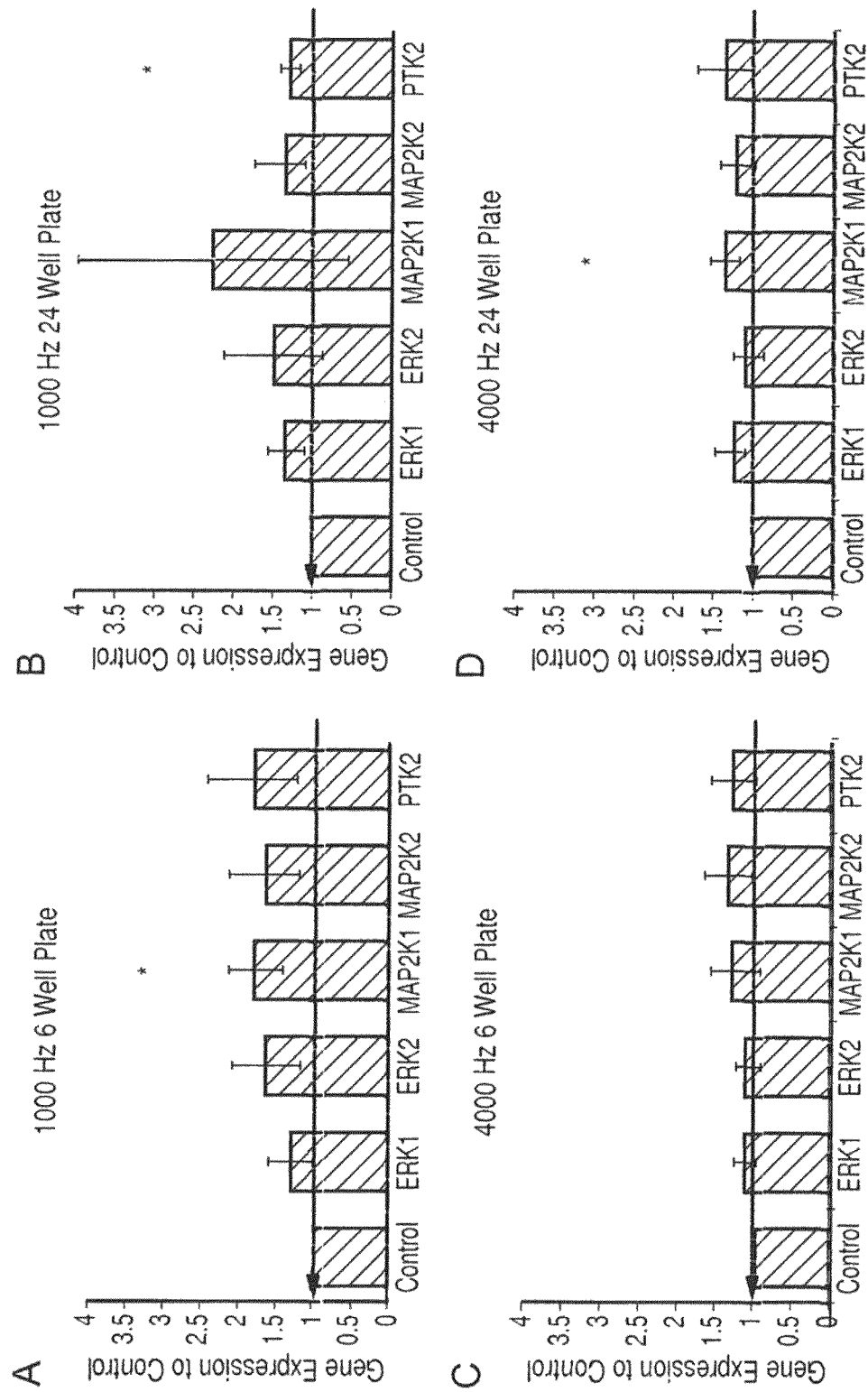
FIGS. 8A to 8D show transcriptional analysis results for another quantitative real time polymerase chain reaction (qRT-PCR) for mRNA gene expression.
FIGS. 8E to 8H are output images following immunostaining for phosphorylated RUNX2 on control and stimulated samples.
FIG. 8I is a graph providing a quantitative representation of pRUNX2 immunostaining intensities from control and stimulated samples.
Figure 8:
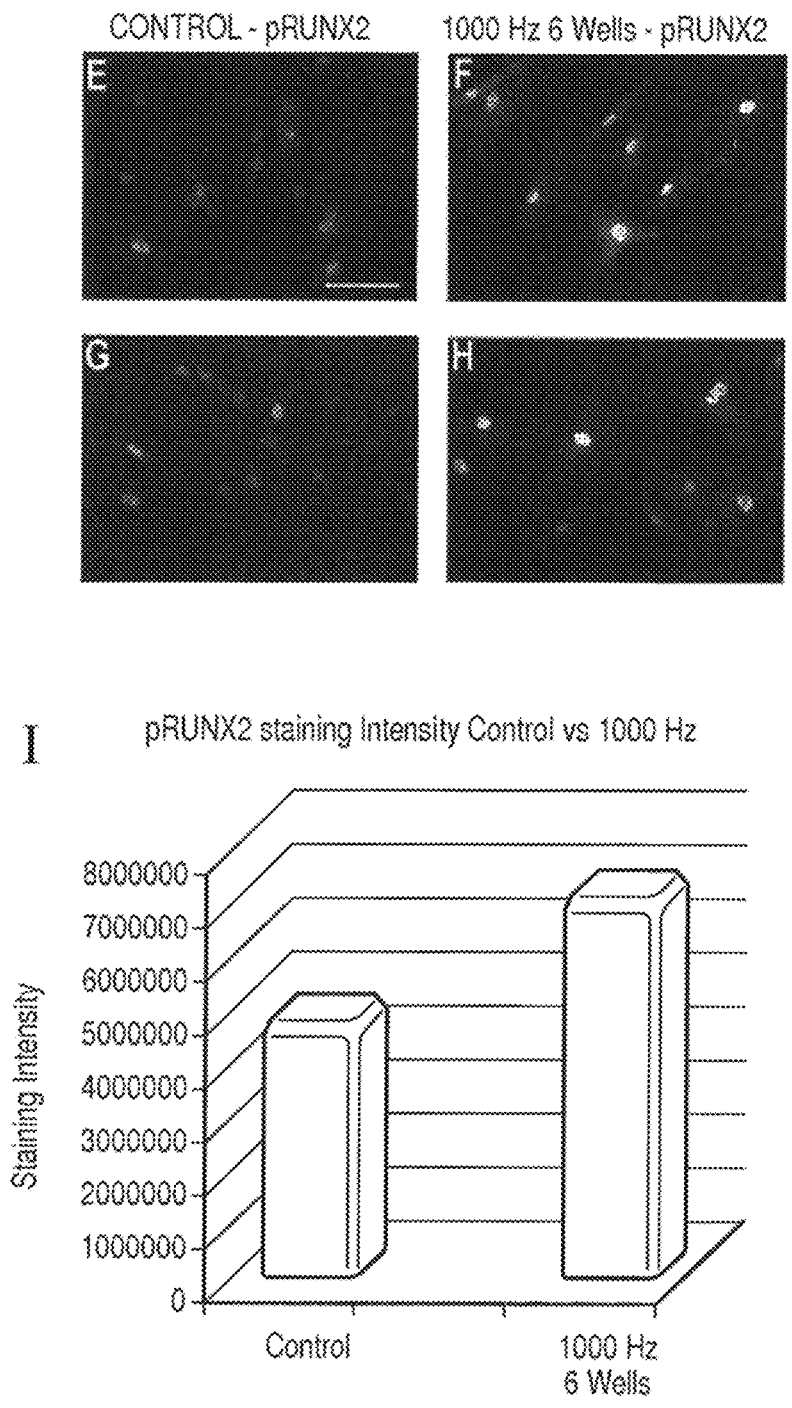

It was noteworthy to understand to some extent, how or by which mechanism osteogenesis would occur using the nanoscale vibrations provided by the bioreactor. Although there undoubtedly are other pathways, it is believed that MEK/MAPK is critical. FIG. 8 shows results following stimulation of MSCs on the vibrational bioreactor for 8 days. The stimulated MSCs were assessed relative to an unstimulated control for expression of genes related to the MAPK/ERK pathway, which is believed to be pivotal for mechanotransductive initiated osteoblastogenesis brought about through vibration, i.e. PTK2 (coding for FAK), ERK 1 and 2, MAP2K1 and MAP2K2. FIG. 8A shows results for MSCs vibrated at a frequency of 1000 Hz in a 6-well plate. FIG. 8B shows results for MSCs vibrated at 1000 Hz in a 24 well plate. FIG. 8C shows results for MSCs vibrated at 4000 Hz in a 6-well plate. FIG. 8D shows results for MSCs vibrated at 4000 Hz in a 24 well plate. All experiments were carried out at an amplitude of 5 V with a 22 nm vertical displacement. The results were obtained using a paired t-test, and show the average of three measurements, with the standard deviation indicated by error bars. The standard deviation for the results marked * was <0.05.

After 8 days of vibration at 1000 Hz and 4000 Hz with cells seeded in a 6 and 24-well plate, qRT-PCR was used to determine the levels of the gene PTK2 encoding for focal adhesion kinase (FAK) relative to an unstimulated control and this was found, through mechanotransduction, to increase. Following the mechanistic cascade, other genes along the MEK/MAPK pathway including extracellular signal regulated kinases (ERK 1 and 2) showed an elevated expression. The activities of ERKs are linked to mitogen activated protein kinases (MAPKs) and subsequently, MAP2K1 and MAP2K2 were also observed to be up regulated with MAP2K1 showing a significant increase (see FIG. 8A).

Figure 6:
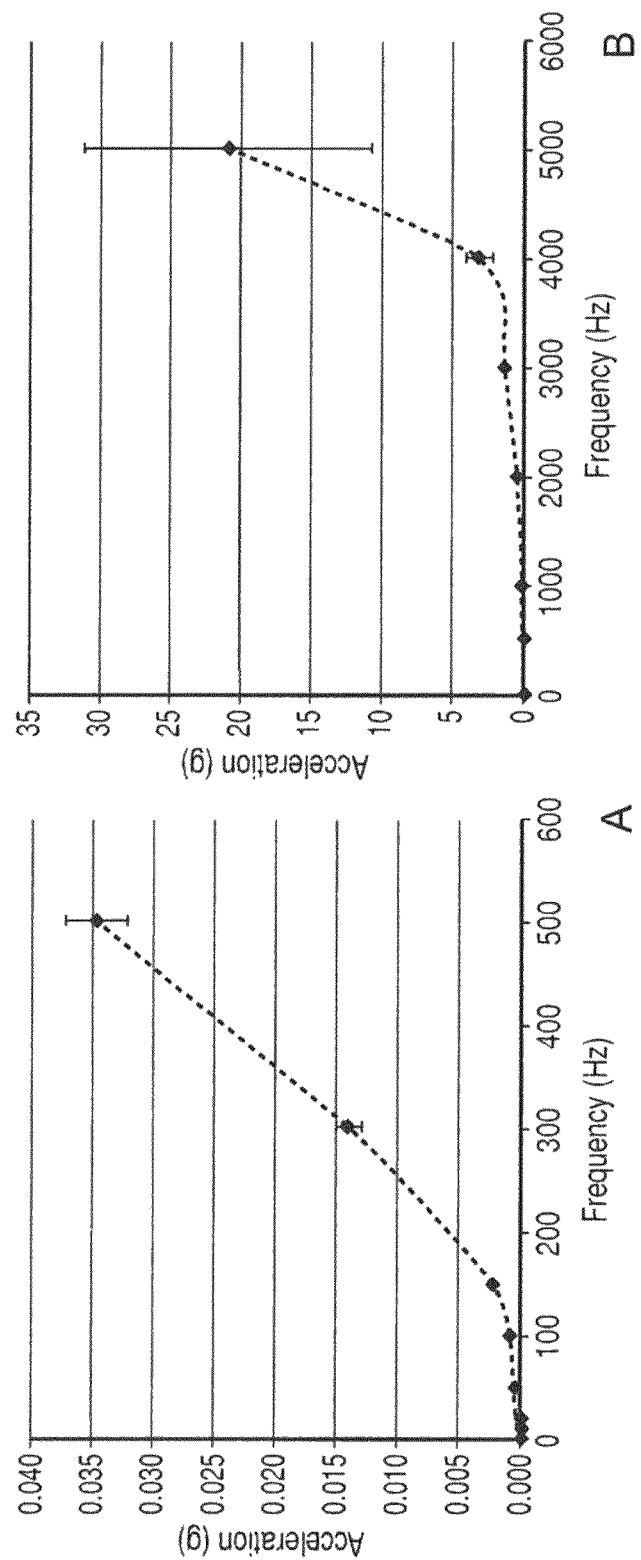
FIGS. 6A and 6B shows the results of a calculation of peak acceleration produced by the bioreactor when amplifier volume is set to 70 over two frequency ranges.

The effector of this mechanistic cascade, i.e. the activated protein form of the osteogenic transcription factor phosphorylated RUNX2, was assessed by immunostaining. FIGS. 8E and 8G show immunostaining images for phosphorylated RUNX2 for controls T1 and T2. These images represent unstimulated or basal levels of proteomic expression of phosphorylated RUNX2. FIGS. 8F and 8H shows immunostaining images for phosphorylated RUNX2 for samples T1 and T2 after stimulation at 1000 Hz in a 6-well plate. Both samples show an increased expression of phosphorulated RUNX2 caused by stimulation using the bioreactor of the invention. The greatest increase is in or around the nucleus of the MSCs [38, 39]. FIG. 6I is a quantitative representation of pRUNX2 immunostaining intensities for a sample vibrated at 1000 Hz for 3 days in a 6-well plate relative to the control with no stimulation.

As was the case above with the osteogenic related genes, the results in FIG. 8A show that the optimum condition of the parameter setting experiments for the increased expression of the MEK/MAPK transcriptomics was from MSCs stimulated in a 6-well plate at a frequency 1000 Hz.

The apparatus of the invention discussed herein also has the ability to stimulate at the nanoscale in three dimensions, a technique that was heretofore unknown and challenging. To demonstrate the effectiveness of the apparatus of the invention in this manner, a 30 biocompatible scaffold that in itself does not initiate osteogenesis was used: collagen type I. The gel was arranged to exhibit a low stiffness, as high stiffness gels can confer osteoinductive properties. For example, pre-calcified bone matrix having a stiffness ~40 kPa has been shown to be osteoinductive to MSCs [43, 44].

Figure 9A:
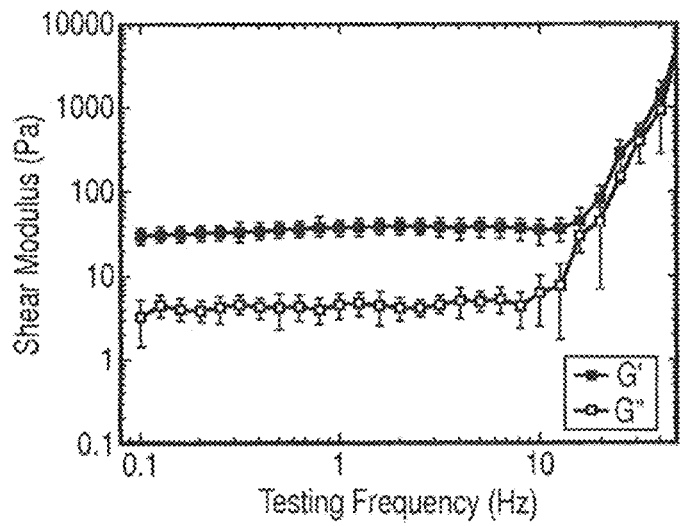
FIG. 9A is a graph showing the results of a rheological assessment for collagen gel without MSCs.
Figure 9B:
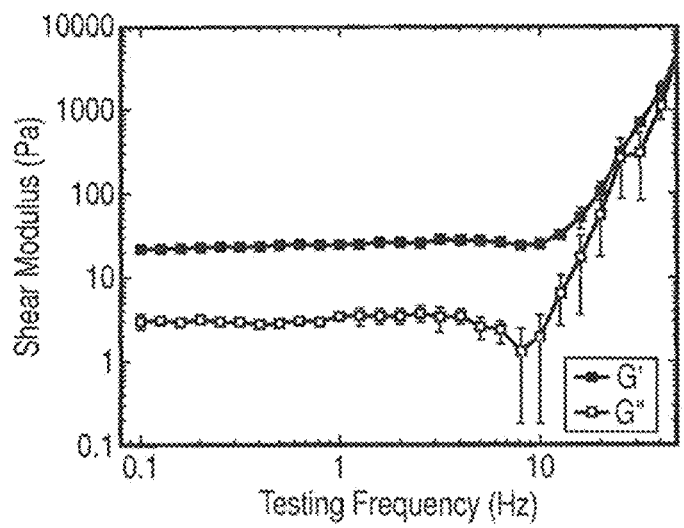
FIG. 9B is a graph showing the results of a rheological assessment for collagen gel seeded with MSCs.

FIGS. 9A and 9B are graphs showing the shear modulus of the gels used in the discussion below without and with MSCs respectively. FIG. 9A shows the results of a rheological assessment for collagen gel without MSCs. Comparison of complex shear moduli values show that a soft gel has been formed rather than a liquid state (i.e. G'>G,). FIG. 9B shows similar data for a collagen gel construct containing 40,000 MG63 osteoblasts/ml (100,000 MSCs for a 2.5 ml sample). Table 3 below shows properties of the gels obtained from the values for shear moduli taken from rheological measurement.

TABLE 3

Material properties of the collagen gels, with and without cells

| | Shear Moduli, G (Pa) | Elastic Moduli, E (Pa) | Bulk Moduli, K (MPa) | Poisson Ratio, v |
|---|---|---|---|---|
| Collagen (no cells) | 36 ± 7.4 | 108 ± 22.2 | 1800 ± 370 | 0.499 |
| Collagen with cells | 24.5 ± 2.3 | 73.5 ± 6.3 | 1225 ± 105 | 0.499 |

The data in FIGS. 9A and 9B show that the gels used had Young's moduli of 108 Pa without cells and 73.5 Pa with cells.

Harmonic response analysis was performed assuming that the gel was within the linear elastic range and incompressible (Poisson ratio v=0.5). For collagen gels under strain, the Poisson ratio describes the absolute ratio between transverse and longitudinal strain. To allow analysis, a Poisson ratio, v, less than 0.5 was chosen. Several values for v were tested for their replication of the interferometric result with an asymptotic increase towards 0.5 increasing the accuracy of the simulation (i.e. ability to transmit a full vibration amplitude of 20 nm). The value used also resulted in a bulk modulus of the same magnitude as water. The bulk modulus describes a material's resistance to uniform compression and that bulk modulus tends to be high in water appears appropriate when considering the water content of collagen.

Figure 9C:
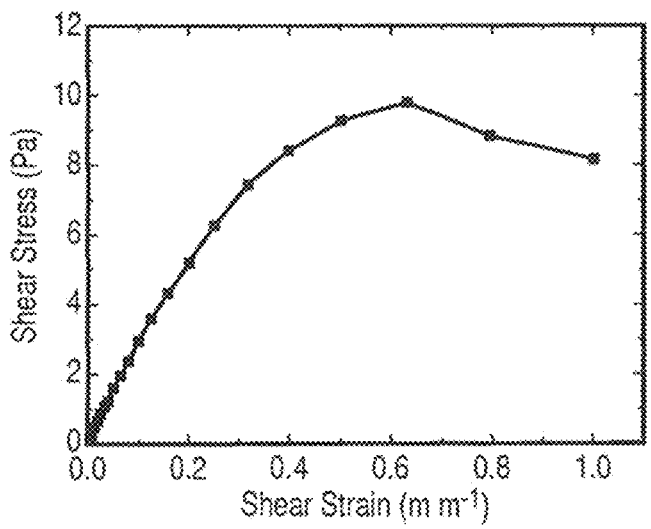
FIG. 9C shows a stress-strain curve for the collagen gel constructs.
Figure 9D:
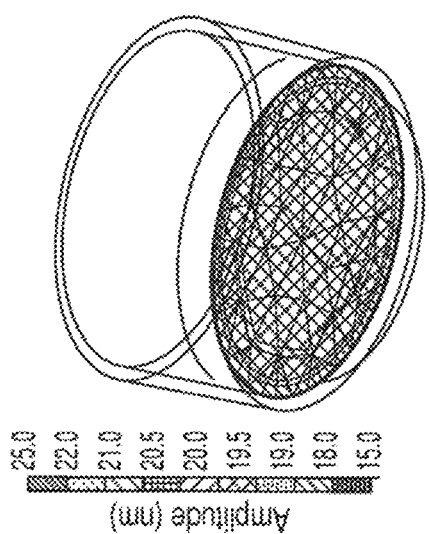
FIG. 9D shows ANSYS deformation modelling of a modelled polystyrene well, replicating one well of a 6-well plate whilst being vibrated at 1000 H with a displacement of 20 nm.
Figure 9E:
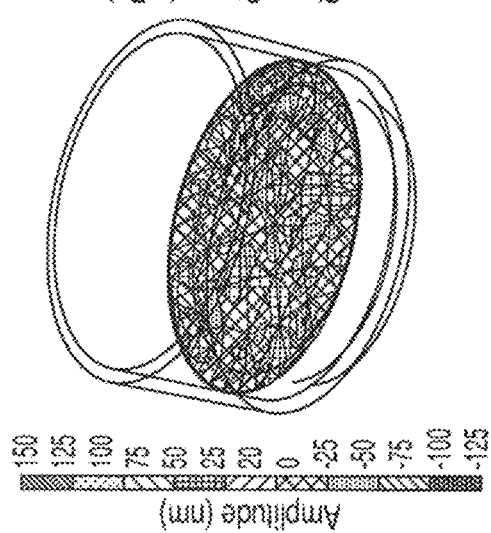
FIG. 9E shows a deformation of a gel that is being vibrated in the modelled polystyrene well of FIG. 9D.

In this example, the sample receiving plates for the gel were modelled as cylindrical polystyrene containers. FIG. 9D shows modelling of the container alone when vibrated at 1000 Hz with 20 nm displacement. There is minimal deformation. FIG. 9E shows modelling of 2.5 ml of gel in the container when vibrated at 1000 Hz with 20 nm displacement. Here the modelling predicts an average amplitude of 29 nm at the edge meniscus and 18 nm at the gel center.

Figure 9F:
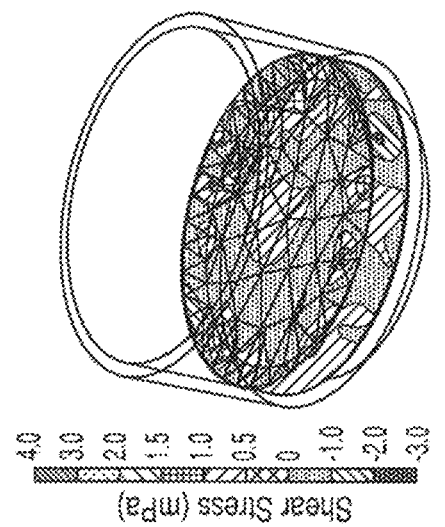
FIG. 9F shows a shear stress for a gel that is being vibrated in the modelled polystyrene well of FIG. 9D.

Using these same modelling parameters, FIG. 9F shows the shear stress and strain within the gel which produced peak values of 3.8 mPa and 1.1×10-4 m/m respectively at 1000 Hz. These values fall below the proportional limit of shear stress and strain which was seen through rheological measurement, shown in FIG. 9C. This supports the validity of a linear analysis for modelling nanovibration at this frequency and suggests that nanokicking produces strains within the linear elastic range of the material. Hence, the viscoelastic properties of the collagen gel are predicted to allow transfer the high frequency vibrations to the cells seeded in 30.

Figure 9G:
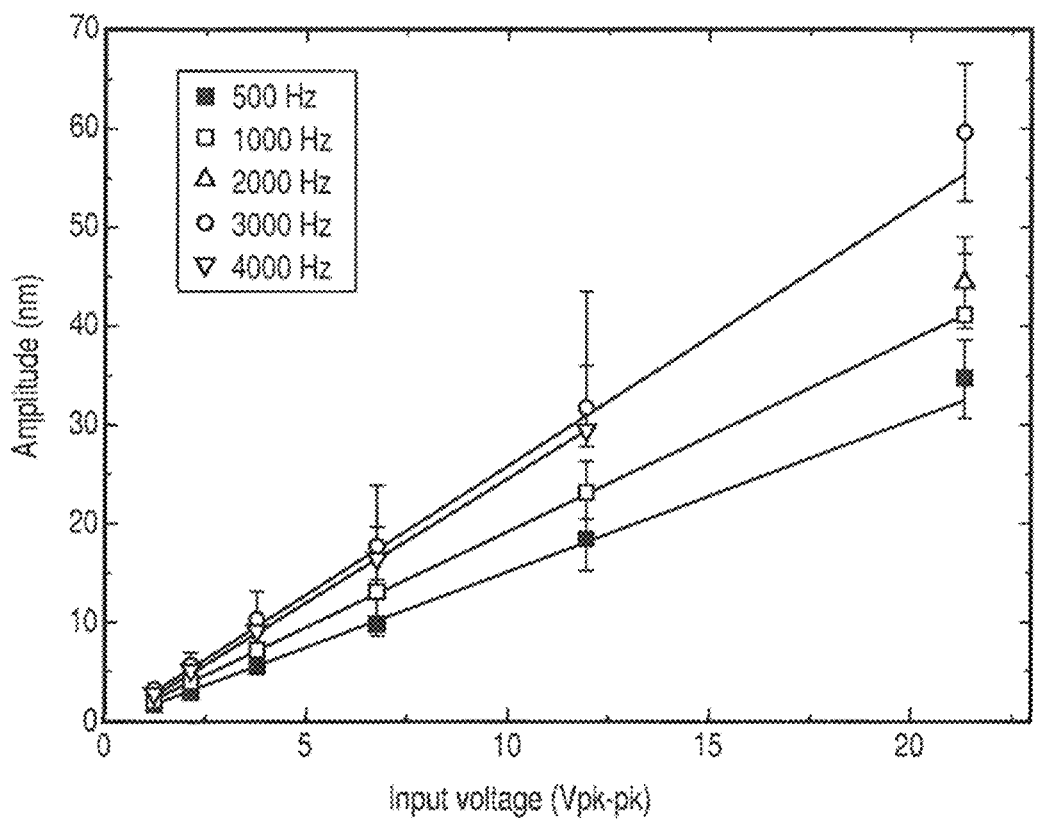
FIG. 9G is a graph showing interferometric calibration of the gel for five vibration frequencies.

Interferometry was again used to confirm predictions. The bioreactor was set up with a 6-well plate and with cells (40,000 MG63 cells/ml) seeded within 2.5 ml collagen gels. Measurements were carried out both at the center and outer edge of the gels. FIG. 9G shows an amplitude calibration for the frequencies examined, in which gel vibration increases linearly with input voltage to the bioreactor.

Figure 9H:
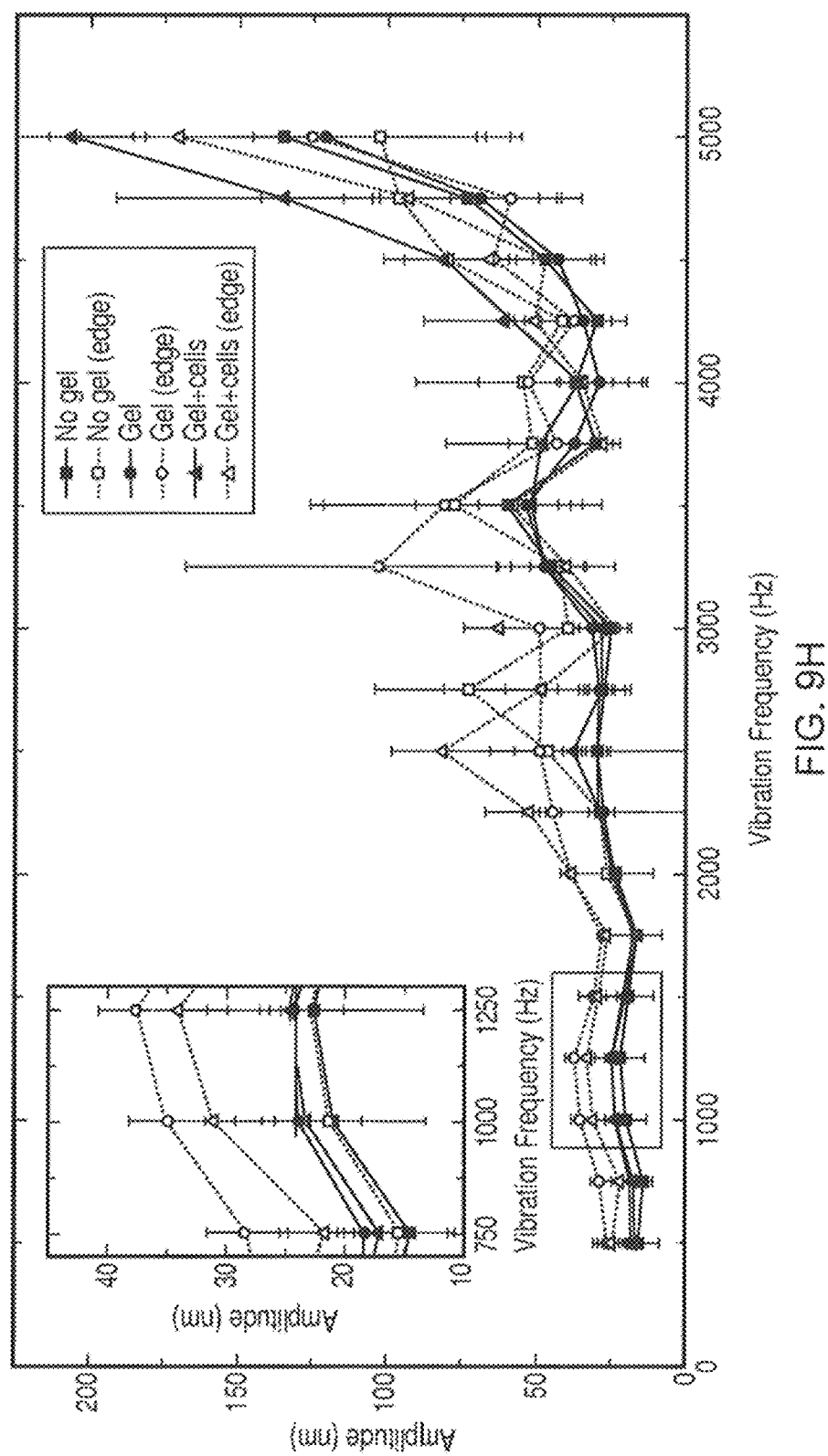
FIG. 9H is a graph showing the nanometer displacement measurements in the range of 500 to 5000 Hz with a set voltage of 12 Vpk-pk.

FIG. 9H shows the gel behavior in terms of frequency. The top surface of the gel was found to follow the surface of the 6 well plate consistently, showing no dampening of the vibration up to 2000 Hz. Samples containing cells did not deviate in response from gels without cells. Within this range there did appear to be increased amplitude at the edge of the gel at the meniscus curvature thus reflecting predicted data. The vibration amplitude seen at the edge of the gel was 35 nm compared to 24 nm at the center for 1000 Hz (see the inset in FIG. 9H).

Resonant frequencies were seen in the region of 2500 Hz, 3500 Hz and 5000 Hz and were observed in both empty and gel filled 6 well plates. This was seen as an increase in vibration amplitude at the outer edge of each well when compared to the center along with a decrease in measurement accuracy. It is noted that if the gel fill is doubled to 5 ml that data indicates that while the gels act similarly in terms of different voltage input, where resonance occurs and middle/edge changes, an amplitude dampening effect is noted.

Results indicate that MSCs within the −100 Pa gels can receive predictable, reproducible nanoscale displacements. This environment is however dramatically different to hard cell culture plastic (such as that used to generate the results of FIGS. 7 and 8) or the much stiffer (e.g. 40 kPa) gels that have been used to stimulate osteogenesis [43, 44]. On this basis, the invention can impart mechanical stimulation to a soft matrix for the purpose of initiating bone formation from MSCs in an otherwise non-inductive environment.

Figure 10A:
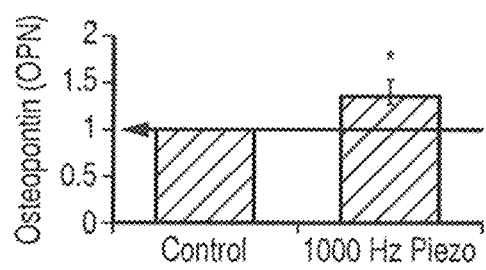
FIGS. 10A and 10B shows results of an osteogenic assessment of nanokicking on bone gene and protein expression.
Figure 10B:
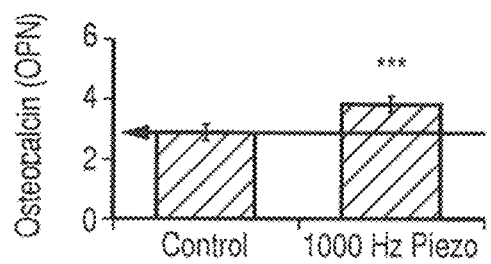

To test this for MSCs in the −100 Pa gels, a range of transcriptional, protein and mineralization assays were performed. FIGS. 10A and 10B show results of an osteogenic assessment of nanokicking on bone gene and protein expression which reveal an increase in osteopontin (OPN) transcripts. For FIG. 10A, MSCs were nanokicked at 1000 Hz for a duration of 21 days in a collagen matrix. Osteopontin (OPN) mRNA was assessed against unstimulated controls using qPCR. In this example, the seeding level was 40,000 MSCs/ml of gel. The results were obtained using a paired t-test, and show the average of three measurements, with the standard deviation indicated by error bars. The standard deviation for the result marked * was <0.05. For FIG. 10B, MSCs were exposed to nanokicking at 1000 Hz for 17 days assessed against unstimulated controls for quantitative protein expression of osteocalcin (OCN) using In Cell Western showing significant increase by nanokicking. In this example, the seeding level was also 40,000 MSCs/ml of gel. The results were obtained using a paired t-test, and show the average of six measurements, with the standard deviation indicated by error bars. The standard deviation for the result marked *** was <0.001.

Figure 11D:
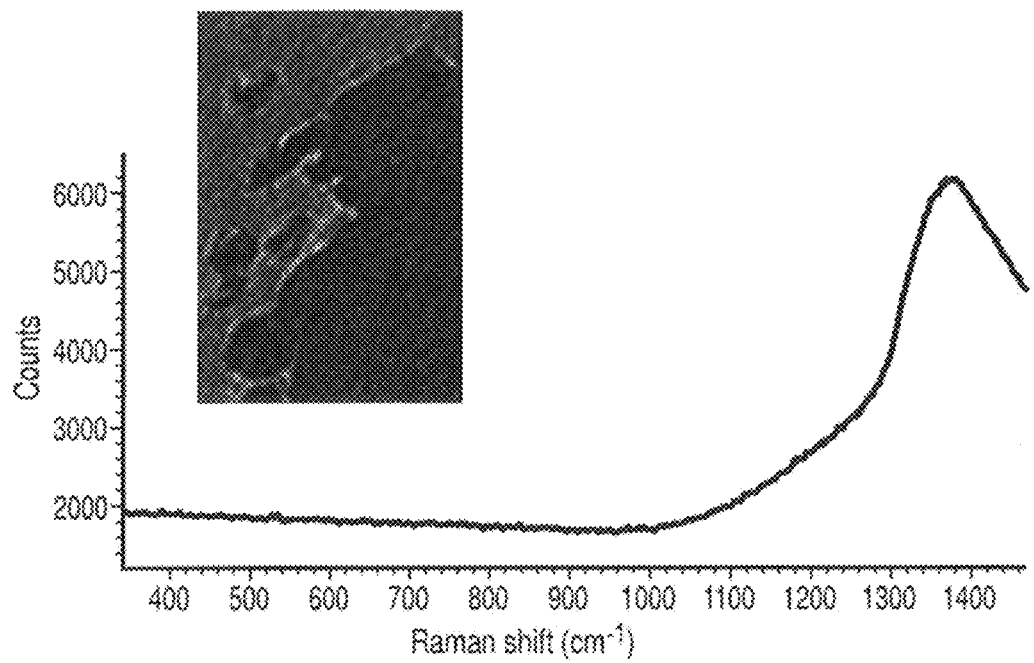
FIG. 11D shows Raman spectra and μCT scan of an unstimulated control sample.

FIGS. 11A to 11E illustrate another example in which the bioreactor delivers vibrations to a three-dimensional sample. FIG. 11A shows a photograph of three samples, each of which comprise a gel (e.g. type I collagen) that has been seeded with 40000 MSCs/ml of gel. The samples comprise 2.5 ml of gel mounted in a respective well of the bioreactor, and are von Kossa stained to show presence of phosphate.

A control sample 900 was not stimulated (vibrated) by the bioreactor. A test sample 900 was vibrated at 1000 Hz for 35 days. A comparative sample (which was also stimulated by the bioreactor in a similar manner to the test sample) included an osteoblast-inducing media (i.e. cell culture food that includes factors that induce MSC differentiation to osteoblasts, such as dexamethasone and ascorbic acid) to provide a positive control.

FIG. 11B is a graph showing the measured intensity from the three samples. The graph shows increased mineralization in the stimulated gels compared with the control.

FIG. 11C shows Raman spectra for bone tissue. This profile was used as a reference standard to characterize the Raman scattering (fingerprint identification region 500 $cm^{-1}$ to 1500 $cm^{-1}$) pattern of bone. The predominant peaks were observed at ~960 $cm^{-1}$ and ~1072 $cm^{-1}$, corresponding to $PO_4^{3-}$ $v_1$ (cortical bone phosphate) and $CO_3^{2-}$— bond stretching respectively.

Figure 11E:
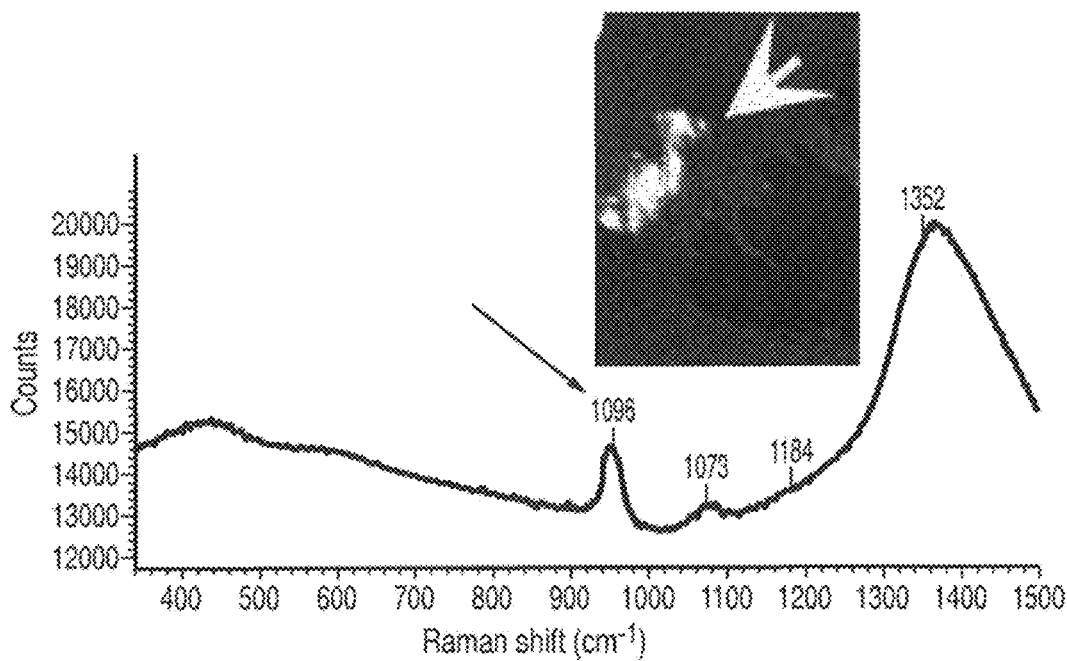
FIG. 11E shows Raman spectra and μCT scan of a stimulated sample.

FIGS. 11D and 11E shows Raman spectra captured for the control and test sample. In FIG. 11D no phosphate peak is seen in the control sample, and μCT scan shows no minerals. However, in FIG. 11E a phosphate peak is present for the test sample, and the μCT scan confirms that mineralization has occurred in the gel. The bioreactor is therefore suitable for use with three-dimensional samples.

The bioreactor discussed above is an important advance that enables scaling up the use of precision mechanical stimuli to induce osteogenesis. The use of finite element modelling and interferometric measurement is a complementary combination in regards to the design and calibration of such a device. The model produced in ANSYS suggested that the bioreactor should have a resonance in the region of 5270.8 Hz whilst maintaining a nano amplitude accuracy of 17% across the device surface at 1000 Hz. The interferometric measurements of the same surface show that in practice an amplitude accuracy greater than 10% can be achieved, i.e. vibration amplitudes of 30±3 nm can be provided across an extended surface.

The data presented herein also shows decreasing amplitude accuracy and increasing average amplitude in both series and parallel wiring configurations above 3000 Hz which suggests that a resonance lies near to 5000 Hz for the top plate. This resonance did not appear for the measurements without the top plate. Throughout the process the highest levels of amplitude accuracy were seen with the parallel wired bioreactor. The increased amplitudes capable with this configuration also suggest that it would be most suitable for investigating the fine tuning of MSC osteogenesis. The limitations of this configuration are again limited accuracy above 3000 Hz and also a limit of 190 nm amplitudes (50 Hz) however the amplitude limitation is strongly dependent on frequency. As seen in the calibration graph, vibration at 5000 Hz no longer follows the similar calibration curve reaching a plateau far earlier than other frequencies which tend to plateau above 100 nm amplitude.

The plateau reached under this configuration is thought to be the result of reaching the slew rate limit of the network amplifier. At higher amplitudes for each frequency, harmonics of the frequency in question will appear on the interferometer FFT output. This can be caused by the sine wave becoming increasingly triangular which would happen upon meeting the slew rate limit.

The level of amplitude accuracy is also useful in characterizing the capable acceleration range of the bioreactor. Assuming the stimulation is a sine wave then the platform is capable of reaching peak acceleration of 20 g. The accuracy at this frequency (5000 Hz) is however questionable which would need to be taken into consideration if comparing to other studies.

The consistency of vibration amplitude whilst using a 24-well plate was found to be drastically lower than that of the 6-well plate. This is reflected in the biology results which show reduced accuracy at times also. The use of the same magnet type leaves the corners of the plate without a solid attachment to the surface therefore altering the magnets used could eliminate this variance both in terms of amplitude and osteogenesis.

Further to this, the biological data from the parameter 10 or specification setting experiments suggests that efficient and reproducible osteoblastic differentiation of MSCs, brought about using our piezo bioreactor, occurs best using a 6-well plate at a frequency of 1000 Hz. It is thought that having a magnet placed under each well relays a consistent uniform displacement mechano-transductively, sensed by the cultured cells. This is not only confirmed by the osteogenic genomic data but also by the MEK/MAPK genomic data which correlates well, providing further confidence. The fact that we have observed an increase in all the genes investigated related to the MEK/MAPK pathway at a transcriptomic level is reassuring as the true biological expression of the MEK/MAPK pathway is observed at the protein level after post translation modification, primarily due to phosphorylation [40]. Furthermore this pathway would more commonly be activated by chemical stimuli through the receptor tyrosine kinase family (RTK)/Ras/Raf, however here we have instead observed a strong response through the FAK. It is also thought that one route may have a suppressive effect on the other suggesting that chemical and mechanical stimulation of osteogenesis may not be complementary [41]. Interestingly, the increase in intensity of the pRUNX2 at the protein level is observed to be strongly centered around the nucleus of the cells. This is logical as one would expect a transcription factor to be located near and around the nucleus, where it can facilitate promotion of the cells genetic machinery.

Whilst 1000 Hz is shows to be a very strong osteoinductive (piezo-vibrational) frequency [36] and therefore an preferred operation mode for the bioreactor of the invention, the invention is not limited to use at this frequency, since there may be other frequencies that can produce similar effects at the same or different amplitudes.

The confirmation that MSCs are mechano-sensitive to motions less than a thousandth of their length scale holds not only promise for new regenerative therapies but also for the development of new fundamental knowledge on mechanotransductive mechanisms. Through the combination of interferometric techniques and osteogenic genomic and proteomic profiling the disclosure herein presents a novel osteogenic-inducing bioreactor.

The ability to produce nano-amplitudes with greater than 10% accuracy over a large range of frequencies and peak accelerations may allow investigation into the fine tuning of biological (stem cell differentiation) mechano-sensitive responses. It is envisaged that an optimum use for this bioreactor would be to provide a ready source of osteoblastic cells or even autologous skeletal tissue in a 30 collagen matrix that could be directly introduced to a specific site in a patient suffering from a skeletal ailment (e.g. osteoporosis, osteoarthritis or bone fracture) which has caused weakened bones.

Furthermore, although not yet investigated, this bioreactor could have as yet unforeseen effects when used to stimulate other cell types within its measured frequency and acceleration ranges. Studies involving suppression of certain cancer cell lines and pathogenic organisms (bacteria) are potential candidates.

REFERENCES

[1] Wysocki, A., et al., Whole-body vibration therapy for osteoporosis: state of the science. Ann Intern Med, 2011. 155(10): p. 680-6, W206-13.

[2] Conrad, C. and R. Huss, Adult stem cell lines in regenerative medicine and reconstructive surgery. Journal of Surgical Research, 2005. 124 (2): p. 201-208.

[3] Dalby, M. J., Cellular response to low adhesion nanotopographies. International Journal of Nanomedicine, 2007. 2 (3): p. 373-381.

[4] Dalby, M. J., et al., Nanotopographical stimulation of mechanotransduction and changes in interphase centromere positioning. Journal of Cellular Biochemistry, 2007. 100(2): p. 326-338.

[5] Dalby, M. J., et al., Genomic expression of mesenchymal stem cells to altered nanoscale topographies. Journal of the Royal Society Interface, 2008. 5(26): p. 1055-1065.

[6] Kingham, E., et al., Nanotopographical cues augment mesenchymal differentiation of human embryonic stem cells. Smal 1, 2013. 9 (12): p. 214 0-51.

[7] Kilian, K. A., et al., Geometric cues for directing the differentiation of mesenchymal stem cells. Proc Natl Acad Sci USA, 2010. 107 (11): p. 4872-7.

[8] Liu, J., et al., Hydrostatic pressures promote initial osteodifferentiation with ERK1/2 not p38 MAPK signaling involved. J Cell Biochem, 2009. 107(2): p. 224-32.

[9] Henstock, J. R., et al., Cyclic hydrostatic pressure stimulates enhanced bone development in the foetal chick femur in vitro. Bone, 2013. 53 (2): p. 468-77.

[10] Kacena, M. A., et al., Experiments with osteoblasts cultured under hypergravity conditions. Microgravity Sci Technol, 2004. 15 (1): p. 28-34.

[11] Zhao, L. G., et al., The MEK5/ERK5 pathway mediates fluid shear stress promoted osteoblast differentiation. Connect Tissue Res, 2014. 55(2): p. 96-102.

[12] Prodanov, L., et al., Substrate nanotexture and hypergravity through centrifugation enhance initial osteoblastogenesis. Tissue Eng Part A, 2013. 19(1-2) p. 114-24.

[13] Luu, Y. K., et al., Mechanical stimulation of mesenchymal stem cell proliferation and differentiation promotes osteogenesis while preventing dietary-induced obesity. J Bone Miner Res, 2009. 24(1): p. 50-61.

[14] Mammoto, A., et al., A mechanosensitive transcriptional mechanism that controls angiogenesis. Nature, 2009. 457(7233): p. 1103-U57.

[15] Ingber, D., How cells (might) sense microgravity. The FASEB Journal, 1999. 13(9001) p. 3-15.

[16] Lan Levengood, S. K., et al., The effect of BMP-2 on micro- and macroscale osteointegration of biphasic calcium phosphate scaffolds with multiscale porosity. Acta Biomater, 2010. 6 (8): p. 3283-91.

[17] Cheng, L., et al., Osteoinduction of calcium phosphate biomaterials in small animals. Mater Sci Eng C Mater Biol Appl, 2013. 33 (3): p. 1254-60.

[18] Chan, O., et al., The effects of microporosity on osteoinduction of calcium phosphate bone graft substitute biomaterials. Acta Biomater, 2012. 8 (7): p. 2788-94.

[19] Habibovic, P., et al., Osteoinduction by biomaterials—physicochemical and structural influences. J Biomed Mater Res A, 2006. 77 (4): p. 747-62.

[20] Berry, C. C., et al., The interaction of human bone marrow cells with nanotopographical features in three dimensional constructs. Journal Of Biomedical Materials Research Part A, 2006. 79A(2): p. 431-439.

[21] Nikukar, H., et al., Osteogenesis of mesenchymal 15 stem cells by nanoscale mechanotransduction. ACS Nano, 2013. 7 (3): p. 2758-67.

[22] Salter, D. M., J. E. Robb, and M. O. Wright, Electrophysiological responses of human bone cells to mechanical stimulation: Evidence for specific integrin function in mechanotransduction. Journal of Bone and Mineral Research, 1997. 12 (7): p. 1133-1141.

[23] Kim, S. H., et al., Erk 1/2 activation in enhanced osteogenesis of human mesenchymal stem cells in poly (lacticglycolic acid) by cyclic hydrostatic pressure. Journal of Biomedical Materials Research Part A, 2007. 80A(4): p. 826-836.

[24] Sawada, Y. and M. P. Sheetz, Force transduction by Triton cytoskeletons. J Cell Biol, 2002. 156(4): p. 609-15.

[25] Vogel, V. and M. Sheetz, Local force and geometry sensing regulate cell functions. Nat Rev Mol Cell Biol, 2006. 7(4): p. 265-75.

[26] Jeong, H. M., et al., Bromopropane compounds inhibit osteogenesis by ERK-dependent Runx2 inhibition in C2Cl2 cells. Archives of Pharmacal Research, 2014. 37(2): p. 276-283.

[27] Xu, D. H., et al., Salvianolic acid B promotes osteogenesis of human mesenchymal stem cells through activating ERK signaling pathway. International Journal of Biochemistry & Cell Biology, 2014. 51: p. 1-9.

[28] Kozawa, O., D. Hatakeyama, and T. Uematsu, Divergent regulation by p44/p42 MAP kinase and p38 MAP kinase of bone morphogenetic protein-4-stimulated osteocalcin synthesis in osteoblasts. Journal of Cellular Biochemistry, 2002. 84(3) p. 583-589.

[29] Kim, I. S., et al., Human mesenchymal stromal cells are mechanosensitive to vibration stimuli. J Dent Res, 2012. 91 (12): p. 1135-40.

[30] Wehland, M., et al., The impact of altered gravity and vibration on endothelial cells during a parabolic flight. Cell Physiol Biochem, 2013. 31 (2-3): p. 432-51.

[31] Gaston, J., et al., The Response of Vocal Fold Fibroblasts and Mesenchymal Stromal Cells to Vibration. PLoS ONE, 2012. 7 (2): p. e30965.

[32] Zhang, C., et al., Effects of mechanical vibration on proliferation and osteogenic differentiation of human periodontal ligament stem cells. Arch Oral Biol, 2012. 57(10) p. 1395-407.

[33] Tirkkonen, L., et al., The effects of vibration loading on adipose stem cell number, viability and differentiation towards bone-forming cells. JR Soc Interface, 2011. 8(65): p. 1736-47.

[34] Ito, Y., et al., Effects of vibration on differentiation of cultured PC12 cells. Biotechnol Bioeng, 2011. 108 (3): p. 592-9.

[35] Curtis, A., et al., Cell Interactions at the Nanoscale: Piezoelectric Stimulation. IEEE Trans Nanobioscience, 2013. 12 (3): p. 247-254.

[36] Gabriel D. Pemberton, S. R., Peter Childs, Habib Nikukar, P Monica Tsimbouri, Nikolaj Gadegaard, Adam S G Curtis & Matthew J Dalby, Nanoscale stimulation of osteoblastogenesis from mesenchymal stem cells: nanotopography and nanokicking. Nanomedicine [In Press], 2014.

[37] Properties of Piezo Actuators—Dynamic Operation. [cited 2014 August]; Available from: http://piceramic.com/piezo-technology/properties-piezoactuators/dynamic-operation.html.

[38] Celil, A. B. and P. G. Campbell, BMP-2 and insulinlike rowth factor-I mediate osterix (Osx) expression in human mesenchymal stem cells via the MAPK and protein kinase D signaling pathways. Journal of Biological Chemistry, 2005. 280(36): p. 31353-31359.

[39] Zhu, F. C., et al., The transcription factor osterix (SP7) regulates BMP6-induced human osteoblast differentiation. Journal of Cellular Physiology, 2012. 227(6): p. 2677-2685.

[40] Burack, W. R. and T. W. Sturgill, The activating dual phosphorylation of MAPK by MEK is nonprocessive. Biochemistry, 1997. 36 (20): p. 5929-5933.

[41] Macagno, J. P., et al., FAK Acts as a Suppressor of RTK-MAP Kinase Signalling in *Drosophila melanogaster* Epithelia and Human Cancer Cells. Plos Genetics, 2014. 10(3).

[42] Miyakoshi, J., The review of cellular effects of a static magnetic field. Science and Technology of Advanced Materials, 2006. 7 (4): p. 305-307.

[43] Engler, A. J., Sen, S., Sweeney, H. L. & Discher, D. E. Matrix elasticity directs stem cell lineage specification. Cell 126, 677-689 (2006).

[44] Wen, J. H., et al. Interplay of matrix stiffness and protein tethering in stem cell differentiation. Nat Mater (2014).

The invention claimed is:

1. An apparatus comprising:
an array of vibration actuators; and
a sample receiving plate vibratably coupled to the array of vibration actuators,
wherein the array of vibration actuators is arranged to vertically oscillate the sample receiving plate at nanoscale amplitudes,
wherein the sample receiving plate has a plurality of sample mounting locations, and wherein the sample receiving plate is configured to:
provide physical engagement to a sample container at each of the plurality of sample mounting locations, and
transmit mechanical vertical vibrations having a substantially uniform nanoscale amplitude across the plurality of sample mounting locations.

2. The apparatus of claim 1, wherein the sample receiving plate is mounted on the array of vibration actuators.

3. The apparatus of claim 1, wherein each vibration actuator is adhered to the sample receiving plate.

4. The apparatus of claim 1, wherein each vibration actuator is part of a respective sample container.

5. The apparatus of claim 1 including a base block, wherein the array of vibration actuators is mounted on an upper surface of the base block, whereby the sample receiving plate is vibratable relative to the base block.

6. The apparatus of claim 5, wherein the array of vibration actuators is arranged to oscillate the sample receiving plate in a direction normal to the upper surface of the base block.

7. The apparatus of claim 1, wherein the sample receiving plate is secured in unbroken physical contact with the sample container.

8. The apparatus of claim 1, wherein the sample receiving plate is magnetically couplable to the sample container.

9. The apparatus of claim 8, wherein the sample receiving plate has a multilayer construction comprising a rigid lower layer and a magnetically sensitive upper layer.

10. The apparatus of claim 9, wherein the upper layer is stainless steel.

11. The apparatus of claim 9, wherein the lower layer is aluminium.

12. The apparatus of claim 1, further comprising a sample container having a plurality of wells for receiving biological tissue samples, wherein the sample container has a magnetic undersurface for engaging the sample receiving plate, whereby the plurality of wells are positioned at the plurality of sample mounting locations.

13. The apparatus of claim 12, wherein the magnetic undersurface comprises a magnetic disk mounted at the base of each of the plurality of wells.

14. The apparatus of claim 1, further comprising a generator arranged to deliver an oscillating drive signal to each vibration actuator.

15. The apparatus of claim 14, wherein each vibration actuator comprises a piezoelectric element, whereby application of the oscillating drive signal across the piezoelectric element causes periodic deformation of the actuator.

16. The apparatus of claim 14, wherein the array of vibration actuators consists of a plurality of actuators connected in series with the generator.

17. The apparatus of claim 16, wherein the generator comprises a voltage source and an oscillator.

18. The apparatus of claim 17, wherein the voltage source has an adjustable output voltage for controlling the vibration amplitude of the array of actuators.

19. The apparatus of claim 14, wherein the array of vibration actuators consists of a plurality of actuators connected to the generator in parallel.

20. The apparatus of claim 19, wherein the generator comprises an amplifier.

21. The apparatus of claim 20, wherein the amplifier has an adjustable amplifier volume for controlling the vibration amplitude of the array of vibration actuators.

* * * * *